US009828635B2

(12) United States Patent
Vincent et al.

(10) Patent No.: US 9,828,635 B2
(45) Date of Patent: Nov. 28, 2017

(54) PREDICTING TUMOR RESPONSE TO ANTI-ERBB3 ANTIBODIES

(71) Applicant: AVEO Pharmaceuticals, Inc., Cambridge, MA (US)

(72) Inventors: Sylvie Vincent, Somerville, MA (US); Kristan Meetze, Lexington, MA (US); Bin Feng, Newton, MA (US); Steven Tyler, Boston, MA (US); Steve Bottega, Cambridge, MA (US); Richard Nicoletti, Southborough, MA (US); Donna McIntosh, Chelmsford, MA (US); Jeno Gyuris, Lincoln, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/349,916

(22) PCT Filed: Oct. 5, 2012

(86) PCT No.: PCT/US2012/058871
§ 371 (c)(1),
(2) Date: Apr. 4, 2014

(87) PCT Pub. No.: WO2013/052745
PCT Pub. Date: Apr. 11, 2013

(65) Prior Publication Data
US 2014/0242597 A1   Aug. 28, 2014

Related U.S. Application Data

(60) Provisional application No. 61/636,183, filed on Apr. 20, 2012, provisional application No. 61/544,206, filed on Oct. 6, 2011.

(51) Int. Cl.
*A61K 39/395* (2006.01)
*C12Q 1/68* (2006.01)
*G01N 33/574* (2006.01)

(52) U.S. Cl.
CPC ...... *C12Q 1/6881* (2013.01); *A61K 39/39558* (2013.01); *G01N 33/574* (2013.01)

(58) Field of Classification Search
None
See application file for complete search history.

(56) References Cited

U.S. PATENT DOCUMENTS

| 5,183,884 A | 2/1993 | Kraus et al. |
| 5,480,968 A | 1/1996 | Kraus et al. |
| 5,820,859 A | 10/1998 | Kraus et al. |
| 5,840,525 A | 11/1998 | Vandlen et al. |
| 5,916,755 A | 6/1999 | Kraus et al. |
| 5,968,511 A | 10/1999 | Akita et al. |
| 6,639,060 B1 | 10/2003 | Kraus et al. |
| 7,285,649 B2 | 10/2007 | Akita et al. |
| 7,705,130 B2 | 4/2010 | Rothe et al. |
| 7,846,440 B2 | 12/2010 | Schoeberl et al. |
| 8,481,687 B2 | 7/2013 | Vincent et al. |
| 9,228,021 B2 | 1/2016 | Vincent et al. |
| 2003/0143539 A1 | 7/2003 | Bertucci et al. |
| 2004/0197332 A1 | 10/2004 | Ullrich et al. |
| 2007/0009972 A1 | 1/2007 | Chao et al. |
| 2007/0122407 A1 | 5/2007 | Akita et al. |
| 2008/0124345 A1 | 5/2008 | Rothe et al. |
| 2009/0061422 A1* | 3/2009 | Linke ............... G01N 33/57415 435/6.14 |
| 2009/0291085 A1* | 11/2009 | Schoeberl ............ A61K 31/337 424/141.1 |
| 2010/0266584 A1 | 10/2010 | Schoeberl et al. |
| 2010/0310557 A1 | 12/2010 | Keyt et al. |
| 2011/0171222 A1 | 7/2011 | Bossenmaier et al. |
| 2011/0256154 A1 | 10/2011 | Vincent et al. |
| 2013/0012465 A1 | 1/2013 | Haslinger et al. |
| 2013/0034565 A1 | 2/2013 | Lindzen et al. |
| 2013/0259867 A1 | 10/2013 | Amler et al. |
| 2013/0288233 A1 | 10/2013 | Murray |

FOREIGN PATENT DOCUMENTS

| CN | 1214695 A | 4/1999 |
| CN | 1835768 A | 9/2006 |
| CN | 101784302 A | 7/2010 |
| WO | WO-94/28133 A1 | 12/1994 |
| WO | WO-97/35885 A1 | 10/1997 |
| WO | WO-99/14323 A1 | 3/1999 |
| WO | WO-02/46467 A2 | 6/2002 |
| WO | WO-2004/008099 A2 | 1/2004 |
| WO | WO-2007/077028 A2 | 7/2007 |
| WO | WO-2008/100624 A2 | 8/2008 |
| WO | WO-2009/027332 A1 | 3/2009 |
| WO | WO-2010/019952 A2 | 2/2010 |
| WO | WO-2010/127181 A1 | 11/2010 |
| WO | WO-2011/022727 A2 | 2/2011 |
| WO | WO-2011/044311 A2 | 4/2011 |
| WO | WO-2012/125864 A2 | 9/2012 |
| WO | WO-2013/025853 A1 | 2/2013 |
| WO | WO-2013/037789 A1 | 3/2013 |

OTHER PUBLICATIONS

Onsum et al, Cancer Research, Apr. 15, 2010; vol. 70, No. 8, Supp. Suppl. 1. Abstract No. 3756.*
Schoeberl et al., 2010, "An ErbB3 Antibody, MM-121, Is Active in Cancers with Ligand-Dependent Activation," *Cancer Res.*, 70(6):2485-2494 and including 18 pages of Supplemental Data.

(Continued)

*Primary Examiner* — Mark Halvorson
(74) *Attorney, Agent, or Firm* — Goodwin Procter LLP

(57) ABSTRACT

A diagnostic method for predicting quantitatively whether a human tumor will be sensitive or resistant to treatment with an ERBB3 inhibitor, e.g, an anti-ERBB3 antibody, is disclosed. The method is based on measurement of NRG1 expression at the RNA level, or at the protein level, in a tissue sample from the tumor.

8 Claims, 24 Drawing Sheets

(56) References Cited

OTHER PUBLICATIONS

Biomarkers Definitions Working Group, 'Biomarkers and Surrogate Endpoints: Preferred Definitions and Conceptual Framework,' Clin Pharmacol Ther, Mar. 2001 (Mar. 2001), 69(3):89-95.

Chen et al., 'An Immunological Approach Reveals Biological Differences between the Two NDF/Heregulin Receptors, ErbB-3 and ErbB-4,' J Biol Chem, Mar. 29, 1996 (Mar. 29, 1996), 271:7620-7629.

Cho WC, 'Contribution of Oncoproteomics to Cancer Biomarker Discovery,' Mol Cancer, Apr. 2, 2007 (Apr. 2, 2007), 6:25-38.

Communication Pursuant to Article 94(3) EPC in European Patent Application No. 12775896 (EP2764364) dated Apr. 1, 2015 (5 pages).

Engelman JA and Cantley LC, 'The Role of the ErbB Family Members in Non-small Cell Lung Cancers Sensitive to Epidermal Growth Factor Receptor Kinase Inhibitors,' Clin Cancer Res, Jul. 15, 2006 (Jul. 15, 2006), 12(14 Pt 2):4372s-6s.

International Search Report and Written Opinion, International Application No. PCT/US2012/058871, dated Mar. 22, 2013 (11 pages).

Kruser TJ and Wheeler DL, 'Mechanisms of Resistance to HER Family Targeting Antibodies,' Exp Cell Res, Apr. 15, 2010 (Apr. 15, 2010), Jan. 11, 2010 (Jan. 11, 2010)(ePub), 316(7):1083-100.

Reply dated Jan. 19, 2016, to Communication Pursuant to Article 94(3) including Reply to Third Party Observations in European Patent Application No. 12775896 (EP2764364) (5 pages).

Ritter CA et al., 'Human Breast Cancer Cells Selected for Resistance to Trastuzumab in vivo Overexpress Epidermal Growth Factor Receptor and ErbB Ligands and Remain Dependent on the ErbB Receptor Network,' Clin Cancer Res, Aug. 15, 2007 (Aug. 15, 2007), 13(16):4909-19.

Sawyers CL, 'The Cancer Biomarker Problem,' Nature, Apr. 3, 2008 (Apr. 3, 2008), 452(7187):548-52.

Schoeberl B et al., 'An ErB3 Antibody, MM-121, is Active in Cancers with Ligand-Dependent Activation,' Cancer Res, Mar. 15, 2010 (Mar. 15, 2010), Mar. 9, 2010 (Mar. 9, 2010)(ePub), 70(6):2485-94.

Schoeberl et al., 'Therapeutically Targeting ErbB3: A Key Node in Ligand-Induced Activation of the ErbB Receptor-PI3K Axis,' Science Signaling, Jun. 30, 2009 (Jun. 30, 2009), 2(77):1-14 (from www.SCIENCESIGNALING.org).

Sergina NV et al., 'Escape from HER-Family Tyrosine Kinase Inhibitor Therapy by the Kinase-Inactive HER3,' Nature, Jan. 25, 2007 (Jan. 25, 2007), Jan. 7, 2007 (Jan. 7, 2007)(ePub), 445(7126):437-41.

Sheng et al., 'An activated ErbB3/NRG1 autocrine loop supports in vivo proliferation in ovarian cancer cells.' Cancer Cell, Mar. 16, 2010 (Mar. 16, 2010), 17(3):298-310.

Sithanandam et al., 'The ERBB3 receptor in cancer and cancer gene therapyERBB3 in cancer,' Cancer Gene Therapy, Jul. 2008 (Jul. 2008), Apr. 11, 2008 (Apr. 11, 2008)(ePub), 15:413-448.

Third Party Observations dated Jan. 16, 2015, filed in European Patent Application No. 12775896 (EP2764364) (2 pages).

Wilson TR et al., 'Neuregulin-1-Mediated Autocrine Signaling Underlies Sensitivity to HER2 Kinase Inhibitors in a Subset of Human Cancers,' Cancer Cell, Aug. 16, 2011 (Aug. 16, 2011), 20(2):158-72.

Zhou BB et al., 'Targeting ADAM-Mediated Ligand Cleavage to Inhibit HER3 and EGFR Pathways in Non-Small Cell Lung Cancer,' Cancer Cell, Jul. 2006 (Jul. 2006), 10(1):39-50.

Third Party Observations submitted in European Patent Application No. 12775896 (EP2764364) dated Aug. 22, 2016 (5 pages).

Third Party Observations submitted in European Patent Application No. 12775896 (EP2764364) dated Jan. 6, 2017 (3 pages).

\* cited by examiner

FIG. 1

Heavy Chain CDR Amino Acid Alignments

| Antibody | CDR1 | | CDR2 | | CDR3 | |
|---|---|---|---|---|---|---|
| AV-203 | DY--AMS | (SEQ ID NO: 1) | TISDGGTYTYYPDSVKG | (SEQ ID NO: 2) | EWG--DYDGFDY | (SEQ ID NO: 3) |
| 04D01 | SH--WLH | (SEQ ID NO: 11) | VLDPSDFYSNYNQNFKG | (SEQ ID NO: 12) | GLL-SGDYAMDY | (SEQ ID NO: 13) |
| 09D03 | TFGLSVG | (SEQ ID NO: 21) | HIWWDDD-KYYNPALKS | (SEQ ID NO: 22) | IG--ADALPFDY | (SEQ ID NO: 23) |
| 11G01 | DH--IIH | (SEQ ID NO: 31) | YIYPRDGYIKYNEKFKG | (SEQ ID NO: 32) | G----YYYAMDY | (SEQ ID NO: 33) |
| 12A07 | SY--WMH | (SEQ ID NO: 40) | MIDPSDVYTNYNPKFKG | (SEQ ID NO: 41) | -----NYSGDY | (SEQ ID NO: 42) |
| 18H02 | TY--GMS | (SEQ ID NO: 47) | WINTYSGVPTYADDFKG | (SEQ ID NO: 48) | GRDGYQVAWFAY | (SEQ ID NO: 49) |
| 22A02 | NY--WMH | (SEQ ID NO: 57) | MIDPSDSYTNYNPKFKG | (SEQ ID NO: 58) | -----NYSGDY | (SEQ ID NO: 42) |

FIG. 2

Complete Heavy Chain Variable Region Amino Acid Alignments

| Antibody | | Sequence | | |
|---|---|---|---|---|
| | | | CDR1 | CDR2 |
| AV-203 | (1) | QVQLVESGGGLVKPGGSLRLSCAASGFTFS | DY--AMS | WIRQAPGKGLEWVS TISDGGTYTYPDSVKGRF |
| 04D01 | (1) | QVQLQQPGAELVRPGTSVKLSCKASGYTFT | SH--WLH | WVKQRPGQGLEWIG VLDPSDFYSNYNQNFKGKA |
| 09D03 | (1) | QVTLKESGPGILRPSQTLSLTCSFSGFSLS | TFGLSVG | WIRQPSGKGLEWLA HIWWDDDK-YYNPALKSRL |
| 11G01 | (1) | QVQLQQSDAELVKPGASVKISCKVSGYTFT | DH--IIH | WMKQRPEQGLEWIG YIYPRDGYIKYNEKFKGKA |
| 12A07 | (1) | QVQLLQPGAELVRPGTSVKLSCKTSGYTFS | SY--WMH | WVKQRPGQGLEWIG MIDPSDVYTNYNPKFKGKA |
| 18H02 | (1) | QIQLVQSGPELKKPGEAVKISCKSSGYTFT | TY--GMS | WVKQAPGRALKWMG WINTYSGVPTYADDFKGRF |
| 22A02 | (1) | QVQLQQPGAELVRPGTSVKLSCKASGYTFT | NY--WMH | WVKQRPGQGLEWIG MIDPSDSYTNYNPKFKGKA |

| Antibody | | Sequence | CDR3 | |
|---|---|---|---|---|
| AV-203 | (69) | TISRDNAKNSLYLQMNSLRAEDTAVYYCAR | EWG--DYDGFDY | WGQGTLVTVSS (SEQ ID NO: 7) |
| 04D01 | (69) | TLTVDTSSSTAYMQLSSLTSEDSAVYYCAR | GLL-SGDYAMDY | WGQGTSVTVSS (SEQ ID NO: 17) |
| 09D03 | (70) | TISKDTSKNQVFLKIANVDTADTATYYCAR | IG--ADALPFDY | WGQGTTLTVSS (SEQ ID NO: 27) |
| 11G01 | (69) | TLTADKSSSTAYMQVNSLTSEDSAVYFCAR | G----YYYAMDY | WGQGTSVTVSS (SEQ ID NO: 36) |
| 12A07 | (69) | TLTVDTSSSTAYMQLSSLTSEDSAVYYCAR | ------NYSGDY | WGQGTTLTVSS (SEQ ID NO: 43) |
| 18H02 | (69) | AFSLESSASTAYLQINNLKNEDTATYFCAR | GRDGYQVAWFAY | WGQGTLVTVSA (SEQ ID NO: 53) |
| 22A02 | (69) | TLTVDTSSSTAYMQLSSLTSEDSAVYYCAR | ------NYSGDY | WGQGTTLTVSS (SEQ ID NO: 59) |

FIG. 3

Light (Kappa) Chain CDR Amino Acid Alignments

| Antibody | CDR1 | | CDR2 | | CDR3 | |
|---|---|---|---|---|---|---|
| AV-203 | RASQEISG----YLS | (SEQ ID NO: 4) | AASTLDS | (SEQ ID NO: 5) | LQYDSYPYT | (SEQ ID NO: 6) |
| 04D01 | RSSQSIVHSNGNTYLE | (SEQ ID NO: 14) | KVSNRFS | (SEQ ID NO: 15) | FQGSYVPWT | (SEQ ID NO: 16) |
| 09D03 | RSSKSLLHSNGNTYLY | (SEQ ID NO: 24) | RMSNLAS | (SEQ ID NO: 25) | MQHLEYPFT | (SEQ ID NO: 26) |
| 11G01 | RSSQSIVHSIGNTYLE | (SEQ ID NO: 34) | KVSNRFS | (SEQ ID NO: 15) | FQGSHVPFT | (SEQ ID NO: 35) |
| 12A07 | RSSQSIVHSNGNTYLE | (SEQ ID NO: 14) | KVSNRFS | (SEQ ID NO: 15) | FQGSYVPWT | (SEQ ID NO: 16) |
| 18H02 | ITSTDIDDD----MN | (SEQ ID NO: 50) | EGNTLRP | (SEQ ID NO: 51) | LQSDNLPYT | (SEQ ID NO: 52) |
| 22A02 | RSSQSIVHSNGNTYLE | (SEQ ID NO: 14) | KVSNRFS | (SEQ ID NO: 15) | FQGSYVPWT | (SEQ ID NO: 16) |

FIG. 4

Complete Light (Kappa) Chain Variable Region Amino Acid Alignments

| Antibody | | CDR1 | CDR2 |
|---|---|---|---|
| AV-203 | (1) | DIQMTQSPSSLSASVGDRVTITCRASQEISG-----YLSWYQQKPGKAPKRLIYAASTLDSGVPSRFSGS |
| 04D01 | (1) | DVLMTQIPLSLPVSLGDQASISCRSSQSIVHSNGNTYLEWYLQKPGQSPKSLIYKVSNRFSGVPDRFSGS |
| 09D03 | (1) | DIVLTQTAPSVPVTPGESVSISCRSSKSLLHSNGNTYLYWFLQRPGQSPQLLIYRMSNLASGVPDRFSGS |
| 11G01 | (1) | DVLMTQTPLSLPVSLGDQASISCRSSQSIVHSIGNTYLEWYLQKPGQSPKLLIYKVSNRFSGVPERFSGS |
| 12A07 | (1) | DVLMTQIPLSLPVSLGDQASISCRSSQSIVHSNGNTYLEWYLQKPGQSPKLLIYKVSNRFSGVPDRFSGS |
| 18H02 | (1) | ETTVTQSPASLSMAIGDKVTIRCITSTDIDDD-----MNWFQQKPGEPPKLLISEGNTLRPGVPSRFSGS |
| 22A02 | (1) | DVLMTQTPLSLPVSLGDQASISCRSSQSIVHSNGNTYLEWYLQKPGQSPKLLIYKVSNRFSGVPDRFSGS |

CDR3

| | | | |
|---|---|---|---|
| AV-203 | (66) | GSGTEFTLTISSLQPEDFATYYCLQYDSYPYTFGQGTKLEIK | (SEQ ID NO: 8) |
| 04D01 | (71) | GSGTDFTLKISRVEAEDLGVYYCFQGSYVPWTFGGGTKLEIK | (SEQ ID NO: 18) |
| 09D03 | (71) | GSGTAFTLRISRVEAEDVGVYYCMQHLEYPFTFGSGTKLEIK | (SEQ ID NO: 28) |
| 11G01 | (71) | GSGTDFTLKISRVEAEDLGVYYCFQGSHVPFTFGSGTKLEIK | (SEQ ID NO: 37) |
| 12A07 | (71) | GSGTDFTLKISRVEAEDLGVYYCFQGSYVPWTFGGGTKLEIK | (SEQ ID NO: 44) |
| 18H02 | (66) | GYGTDFIFTIENMLSEDVADYYCLQSDNLPYTFGGGTKLEIK | (SEQ ID NO: 54) |
| 22A02 | (71) | GSGTDFTLKISRVEAEDLGVYYCFQGSYVPWTFGGGTKLEIK | (SEQ ID NO: 60) |

```
  1 mdmrvpaqll glllllwlrga rcqvqlvesg gglvkpggsl rlscaasgft fsdyamswir
 61 qapgkglewv stisdggtyt yypdsvkgrf tisrdnakns lylqmnslra edtavyycar
121 ewgdydgfdy wgqgtlvtvs sastkgpsvf plapssksts ggtaalgclv kdyfpepvtv
181 swnsgaltsg vhtfpavlqs sglyslssvv tvpssslgtq tyicnvnhkp sntkvdkrve
241 pkscdkthtc ppcpapellg gpsvflfppk pkdtlmisrt pevtcvvvdv shedpevkfn
301 wyvdgvevhn aktkpreeqy nstyrvvsvl tvlhqdwlng keykckvsnk alpapiekti
361 skakgqprep qvytlppsre emtknqvslt clvkgfypsd iavewesngq pennykttpp
421 vldsdgsffl yskltvdksr wqqgnvfscs vmhealhnhy tqkslslspg k
(SEQ ID NO: 9)
```

(B)

```
  1 mdmrvpaqll glllllwlrga rcdiqmtqsp sslsasvgdr vtitcrasqe isgylswyqq
 61 kpgkapkrli yaastldsgv psrfsgsgsg teftltissl qpedfatyyc lqydsypytf
121 gqgtkleikr tvaapsvfif ppsdeqlksg tasvvcllnn fypreakvqw kvdnalqsgn
181 sqesvteqds kdstyslsst ltlskadyek hkvyacevth qglsspvtks fnrgec
(SEQ ID NO: 10)
```

```
  1    mgwsciivll vstatgvhsq vqlqqpgael vrpgtsvkls ckasgytfts hwlhwvkqrp
 61    gqglewigvl dpsdfysnyn qnfkgkatlt vdtssstaym qlssltseds avyycargll
121    sgdyamdywg qgtsvtvssa kttppsvypl apgsaaqtns mvtlgclvkg yfpepvtvtw
181    nsgslssgvh tfpavlqsdl ytlsssvtvp sstwpsqtvt cnvahpasst kvdkkivprd
241    cgckpcictv pevssvfifp pkpkdvltit ltpkvtcvvv diskddpevq fswfvddvev
301    htaqtqpree qfnstfrsvs elpimhqdwl ngkefkcrvn saafpapiek tisktkgrpk
361    apqvytippp keqmakdkvs ltcmitdffp editvewqwn gqpaenyknt qpimdtdgsy
421    fvysklnvqk snweagntft csvlheglhn hhtekslshs pgk
(SEQ ID NO: 19)
```

(B)

```
  1    mklpvrllvl mfwipasssd vlmtqiplsl pvslgdqasi scrssqsivh sngntylewy
 61    lqkpgqspks liykvsnrfs gvpdrfsgsg sgtdftlkis rveaedlgvy ycfqgsyvpw
121    tfgggtklei kradaaptvs ifppsseqlt sggasvvcfl nnfyprdinv kwkidgserq
181    ngvlnswtdq dskdstysms stltltkdey erhnsytcea thktstspiv ksfnrnec
(SEQ ID NO: 20)
```

```
  1    mgrltssfll livpayvlsq vtlkesgpgi lrpsqtlslt csfsgfslst fglsvgwirq
 61    psgkglewla hiwwdddkyy npalksrlti skdtsknqvf lkianvdtad tatyycarig
121    adalpfdywg qgttltvssa kttppsvypl apgcgdttgs svtsgclvkg yfpepvtvtw
181    nsgslsssvh tfpallqsgl ytmsssvtvp sstwpsqtvt csvahpasst tvdkklepsg
241    pistinpcpp ckechkcpap nleggpsvfi fppnikdvlm isltpkvtcv vvdvseddpd
301    vqiswfvnnv evhtaqtqth redynstirv vstlpiqhqd wmsgkefkck vnnkdlpspi
361    ertiskikgl vrapqvytlp ppaeqlsrkd vsltclvvgf npgdisvewt snghteenyk
421    dtapvldsdg syfiysklnm ktskwektds fscnvrhegl knyylkktis rspgk
(SEQ ID NO: 29)
```

(B)

```
  1    mrclaeflgl lvlwipgaig divltqtaps vpvtpgesvs iscrssksll hsngntylyw
 61    flqrpgqspq lliyrmsnla sgvpdrfsgs gsgtaftlri srveaedvgv yycmqhleyp
121    ftfgsgtkle ikradaaptv sifppsseql tsggasvvcf lnnfyprdin vkwkidgser
181    qngvlnswtd qdskdstysm sstltltkde yerhnsytce athktstspi vksfnrnec
(SEQ ID NO: 30)
```

```
  1    mewswvslff lsvttgvhsq vqlqqsdael vkpgasvkis ckvsgytftd hiihwmkqrp
 61    eqglewigyi yprdgyikyn ekfkgkatlt adkssstaym qvnsltseds avyfcargyy
121    yamdywgqgt svtvssaktt ppsvyplapg saaqtnsmvt lgclvkgyfp epvtvtwnsg
181    slssgvhtfp avlqsdlytl sssvtvpsst wpsqtvtcnv ahpasstkvd kkivprdcgc
241    kpcictvpev ssvfifppkp kdvltitltp kvtcvvvdis kddpevqfsw fvddvevhta
301    qtqpreeqfn stfrsvselp imhqdwlngk efkcrvnsaa fpapiektis ktkgrpkapq
361    vytipppkeq makdkvsltc mitdffpedi tvewqwngqp aenykntqpi mdtdgsyfvy
421    sklnvqksnw eagntftcsv lheglhnhht ekslshspgk
(SEQ ID NO: 38)
```

(B)

```
  1    mklpvrllvl mfwipasrsd vlmtqtplsl pvslgdqasi scrssqsivh signtylewy
 61    lqkpgqspkl liykvsnrfs gvperfsgsg sgtdftlkis rveaedlgvy ycfqgshvpf
121    tfgsgtklei kradaaptvs ifppsseqlt sggasvvcfl nnfypkdinv kwkidgserq
181    ngvlnswtdq dskdstysms stltltkdey erhnsytcea thktstspiv ksfnrnec
(SEQ ID NO: 39)
```

```
  1   mgwsciivll vstatcvhsq vqllqpgael vrpgtsvkls cktsgytfss ywmhwvkqrp
 61   gqglewigmi dpsdvytnyn pkfkgkatlt vdtssstaym qlssltseds avyycarnys
121   gdywgqgttl tvssakttpp svyplapgsa aqtnsmvtlg clvkgyfpep vtvtwnsgsl
181   ssgvhtfpav lqsdlytlss svtvpsstwp sqtvtcnvah passtkvdkk ivprdcgckp
241   cictvpevss vfifppkpkd vltitltpkv tcvvvdiskd dpevqfswfv ddvevhtaqt
301   qpreeqfnst frsvselpim hqdwlngkef kcrvnsaafp apiektiskt kgrpkapqvy
361   tipppkeqma kdkvsltcmi tdffpeditv ewqwngqpae nykntqpimd tdgsyfvysk
421   lnvqksnwea gntftcsvlh eglhnhhtek slshspgk
(SEQ ID NO: 45)
```

(B)

```
  1   mklpvrllvl mfwipasssd vlmtqiplsl pvslgdqasi scrssqsivh sngntylewy
 61   lqkpgqspkl liykvsnrfs gvpdrfsgsg sgtdftlkis rveaedlgvy ycfqgsyvpw
121   tfgggtklei kradaaptvs ifppsseqlt sggasvvcfl nnfyprdinv kwkidgserq
181   ngvlnswtdq dskdstysms stltltkdey erhnsytcea thktstspiv ksfnrnec
(SEQ ID NO: 46)
```

```
  1 mgwlwnllfl maaaqsaqaq iqlvqsgpel kkpgeavkis ckssgytftt ygmswvkqap
 61 gralkwmgwi ntysgvptya ddfkgrfafs lessastayl qinnlknedt atyfcargrd
121 gyqvawfayw gqgtlvtvsa akttppsvyp lapgsaaqtn smvtlgclvk gyfpepvtvt
181 wnsgslssgv htfpavlqsd lytlsssvtv psstwpsqtv tcnvahpass tkvdkkivpr
241 dcgckpcict vpevssvfif ppkpkdvlti tltpkvtcvv vdiskddpev qfswfvddve
301 vhtaqtqpre eqfnstfrsv selpimhqdw lngkefkcrv nsaafpapie ktisktkgrp
361 kapqvytipp pkeqmakdkv sltcmitdff peditvewqw ngqpaenykn tqpimdtdgs
421 yfvysklnvq ksnweagntf tcsvlheglh nhhtekslsh spgk
(SEQ ID NO: 55)
```

(B)

```
  1 mfslalllsl lllcvsdsra ettvtqspas lsmaigdkvt ircitstdid ddmnwfqqkp
 61 geppkllise gntlrpgvps rfsgsgygtd fiftienmls edvadyyclq sdnlpytfgg
121 gtkleikrad aaptvsifpp sseqltsgga svvcflnnfy prdinvkwki dgserqngvl
181 nswtdqdskd stysmsstlt ltkdeyerhn sytceathkt stspivksfn rnec
(SEQ ID NO: 56)
```

```
  1 mgwsciivll vstatgvhsq vqlqqpgael vrpgtsvkls ckasgytftn ywmhwvkqrp
 61 gqglewigmi dpsdsytnyn pkfkgkatlt vdtssstaym qlssltseds avyycarnys
121 gdywgqgttl tvssakttpp svyplapgsa aqtnsmvtlg clvkgyfpep vtvtwnsgsl
181 ssgvhtfpav lqsdlytlss svtvpsstwp sqtvtcnvah passtkvdkk ivprdcgckp
241 cictvpevss vfifppkpkd vltitltpkv tcvvvdiskd dpevqfswfv ddvevhtaqt
301 qpreeqfnst frsvselpim hqdwlngkef kcrvnsaafp apiektiskt kgrpkapqvy
361 tipppkeqma kdkvsltcmi tdffpeditv ewqwngqpae nykntqpimd tdgsyfvysk
421 lnvqksnwea gntftcsvlh eglhnhhtek slshspgk
(SEQ ID NO: 61)
```

(B)

```
  1   mklpvrllvl mfwipasssd vlmtqtplsl pvslgdqasi scrssqsivh sngntylewy
 61   lqkpgqspkl liykvsnrfs gvpdrfsgsg sgtdftlkis rveaedlgvy ycfqgsyvpw
121   tfgggtklei kradaaptvs ifppsseqlt sggasvvcfl nnfyprdinv kwkidgserq
181   ngvlnswtdq dskdstysms stltltkdey erhnsytcea thktstspiv ksfnrnec
(SEQ ID NO: 62)
```

PREDICTING TUMOR RESPONSE TO ANTI-ERBB3 ANTIBODIES

CROSS-REFERENCE TO RELATED APPLICATIONS

This application is the U.S. National Stage of International (PCT) Patent Application No. PCT/US2012/058871, filed Oct. 5, 2012, and published under PCT Article 21(2) in English, which claims the benefit of and priority to U.S. provisional application Ser. No. 61/636,183, filed Apr. 20, 2012 and U.S. provisional application Ser. No. 61/544,206, filed Oct. 6, 2011; the entire contents of each application are incorporated herein by reference.

FIELD OF THE INVENTION

The field of the invention is molecular biology, oncology, and clinical diagnostics.

BACKGROUND

Most cancer drugs are effective in some patients, but not in others. This results from genetic variation among tumors, and can be observed even among tumors within the same patient. Variable patient response is particularly pronounced with respect to targeted therapeutics. Therefore, the full potential of targeted therapies cannot be realized without suitable tests for determining which patients will benefit from which drugs. According to the National Institutes of Health (NIH), the term "biomarker" is defined as "a characteristic that is objectively measured and evaluated as an indicator of normal biologic or pathogenic processes or pharmacological response to a therapeutic intervention." (Biomarkers Definitions Working Group, 2001, *Clin. Pharmacol. Ther.* 69:89-95)

The development of improved diagnostics based on the discovery of biomarkers has the potential to accelerate new drug development by identifying, in advance, those patients most likely to show a clinical response to a given drug. This would significantly reduce the size, length and cost of clinical trials. Technologies such as genomics, proteomics and molecular imaging currently enable rapid, sensitive and reliable detection of specific gene mutations, expression levels of particular genes, and other molecular biomarkers. In spite of the availability of various technologies for molecular characterization of tumors, the clinical utilization of cancer biomarkers remains largely unrealized because few cancer biomarkers have been discovered. For example, a recent review article states:

There is a critical need for expedited development of biomarkers and their use to improve diagnosis and treatment of cancer. (Cho, 2007, *Molecular Cancer* 6:25)

Another recent review article on cancer biomarkers contains the following comments:

The challenge is discovering cancer biomarkers. Although there have been clinical successes in targeting molecularly defined subsets of several tumor types—such as chronic myeloid leukemia, gastrointestinal stromal tumor, lung cancer and glioblastoma multiforme—using molecularly targeted agents, the ability to apply such successes in a broader context is severely limited by the lack of an efficient strategy to evaluate targeted agents in patients. The problem mainly lies in the inability to select patients with molecularly defined cancers for clinical trials to evaluate these exciting new drugs. The solution requires biomarkers that reliably identify those patients who are most likely to benefit from a particular agent. (Sawyers, 2008, *Nature* 452:548-552, at 548)

Comments such as the foregoing illustrate the recognition of a need for the discovery of clinically useful biomarkers and diagnostic methods based on such biomarkers.

There are three distinct types of cancer biomarkers: (1) prognostic biomarkers, (2) predictive biomarkers, and (3) pharmacodynamic (PD) biomarkers. A prognostic biomarker is used to classify a cancer, e.g., a solid tumor, according to aggressiveness, i.e., rate of growth and/or metastasis, and refractiveness to treatment. This is sometimes called distinguishing "good outcome" tumors from "poor outcome" tumors. A predictive biomarker is used to assess the probability that a particular patient will benefit from treatment with a particular drug. For example, patients with breast cancer in which the ERBB2 (HER2) gene is amplified are likely to benefit from treatment with trastuzumab (HERCEPTIN®), whereas patients without ERBB2 gene amplification are unlikely to benefit from treatment with trastuzumab. A PD biomarker is an indication of the effect(s) of a drug on its molecular target while the patient is taking the drug. Accordingly, PD biomarkers often are used to guide dosage level and dosing frequency, during the early stages of clinical development of a new drug. For a discussion of cancer biomarkers, see, e.g., Sawyers, 2008, *Nature* 452:548-552.

Tumors driven by EGFR or HER2 often respond to treatment with inhibitors of EGFR or HER2, but these tumors invariably develop resistance to these inhibitors. At least one mechanism of acquired resistance to anti-EGFR or anti-HER2 treatment is activation of ERBB3 (also known as HER3) signaling. See, e.g., Engelman et al., 2006, *Clin. Cancer Res.* 12:4372; Ritter et al., 2007, *Clin. Cancer Res.* 13:4909; Sergina et al., 2007, *Nature* 445:437. NRG1-induced activation of HER2-ERBB3 heterodimers also has been associated with resistance to EGFR inhibitors (Zhou et al., 2006, *Cancer Cell* 10:39). Thus, ERBB3 plays an important role in development of drug resistance, as well as being involved in tumor initiation and maintenance, through its heterodimerization with EGFR and HER2. Consequently, there has been interest in development of ERBB3 inhibitors, especially anti-ERBB3 antibodies, since ERBB3 lacks kinase activity.

As with other types of targeted therapy, some, but not all, tumors respond to anti-ERBB3 therapy. Therefore, there is a need for diagnostic methods based on predictive biomarkers that can be used to identify patients with tumors that are likely (or unlikely) to respond to treatment with an ERBB3 inhibitor such as an anti-ERBB3 antibody.

SUMMARY

The invention is based, in part, on the discovery that neuregulin-1 (NRG1) expression in a tissue sample from a mammalian tumor (e.g., a human tumor) correlates with sensitivity of the tumor to treatment with an ERBB3 inhibitor, e.g., an anti-ERBB3 antibody. Surprisingly, it has been discovered that the correlation is strong enough that measurement of NRG1 expression alone is sufficient for useful classification of a tumor as sensitive or resistant to treatment with an ERBB3 inhibitor. Accordingly, the invention provides a method of identifying a tumor that is sensitive to treatment with an ERBB3 inhibitor. The method includes: (a) measuring NRG1 gene expression in a tissue sample from the tumor, thereby determining an NRG1 score; and (b)

comparing the NRG1 score against a threshold score defined by a threshold determination analysis. An NRG1 score equal to or above the threshold score indicates that the tumor is likely to be sensitive to treatment with an ERBB3 inhibitor, e.g., an anti-ERBB3 antibody. Alternatively, an NRG1 score below the threshold indicates that the tumor is likely to be resistant to treatment with an ERBB3 inhibitor, e.g., an anti-ERBB3 antibody. In certain embodiments, the method is not based on the expression of any other gene than NRG1.

Measurement of NRG1 expression can be at the protein level, e.g., by immunohistochemistry (IHC) involving a chromophore or fluorophore conjugated to an anti-NRG1 antibody. Alternatively, measurement of NRG1 expression can be at the RNA level, e.g., by measuring the level of mRNA encoding NRG1, e.g., by quantitative PCR or microarray. The threshold determination analysis can include a receiver operator characteristic curve analysis. Methods of the invention are useful for testing various types of tumors, e.g., solid tumors, including, e.g., breast tumors, lung tumors, kidney tumors, colorectal tumors, head and neck tumors, esophageal tumors, ovarian tumors, and pancreatic tumors.

BRIEF DESCRIPTION OF THE DRAWINGS

FIG. 1 is a schematic diagram showing the $CDR_{H1}$, $CDR_{H2}$, and $CDR_{H3}$ sequences (Kabat definition) of the immunoglobulin heavy chain variable regions sequences for the anti-ERBB3 antibodies denoted as AV-203, 04D01, 09D03, 11G01, 12A07, 18H02 and 22A02 (which correspond to the boxed regions in FIG. 2).

FIG. 2 is a schematic diagram showing the amino acid sequence of the complete immunoglobulin heavy chain variable region for the anti-ERBB3 antibodies denoted as AV-203, 04D01, 09D03, 11G01, 12A07, 18H02 and 22A02. The amino acid sequences for each antibody are aligned against one another, and Complementary Determining Sequences (CDR) (Kabat definition), $CDR_{H1}$, $CDR_{H2}$, and $CDR_{H3}$, are identified in boxes. The unboxed sequences represent framework (FR) sequences.

FIG. 3 is a schematic diagram showing the $CDR_{L1}$, $CDR_{L2}$, and $CDR_{L3}$ sequences (Kabat definition) of the immunoglobulin light chain variable regions sequences for the anti-ERBB3 antibodies denoted as AV-203, 04D01, 09D03, 11G01, 12A07, 18H02 and 22A02 (which correspond to the boxed regions in FIG. 4).

FIG. 4 is a schematic diagram showing the amino acid sequence of the complete immunoglobulin light chain variable region for the anti-ERBB3 antibodies denoted as AV-203, 04D01, 09D03, 11G01, 12A07, 18H02 and 22A02. The amino acid sequences for each antibody are aligned against one another, and Complementary Determining Sequences (CDR) (Kabat definition), $CDR_{L1}$, $CDR_{L2}$, and $CDR_{L3}$, are identified in boxes. The unboxed sequences represent framework (FR) sequences.

FIG. 5 provides the amino acid sequence defining the (A) full length AV-203 immunoglobulin heavy chain and (B) the full length AV-203 immunoglobulin light chain.

FIG. 6 provides the amino acid sequence defining the (A) full length 04D01 immunoglobulin heavy chain and (B) the full length 04D01 immunoglobulin light chain.

FIG. 7 provides the amino acid sequence defining the (A) full length 09D03 immunoglobulin heavy chain and (B) the full length 09D03 immunoglobulin light chain.

FIG. 8 provides the amino acid sequence defining the (A) full length 11G01 immunoglobulin heavy chain and (B) the full length 11G01 immunoglobulin light chain.

FIG. 9 provides the amino acid sequence defining the (A) full length 12A07 immunoglobulin heavy chain and (B) the full length 12A07 immunoglobulin light chain.

FIG. 10 provides the amino acid sequence defining the (A) full length 18H02 immunoglobulin heavy chain and (B) the full length 18H02 immunoglobulin light chain.

FIG. 11 provides the amino acid sequence defining the (A) full length 22A02 immunoglobulin heavy chain and (B) the full length 22A02 immunoglobulin light chain.

DETAILED DESCRIPTION OF THE INVENTION

Definitions

Figure 12:
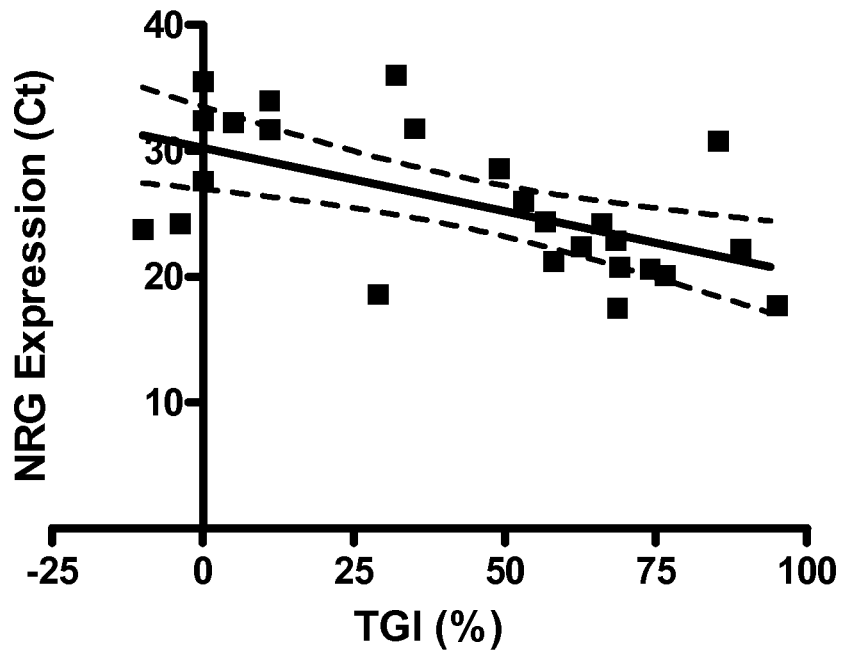
FIG. 12 is a scatter plot with a linear regression trend line showing the relationship between the in vivo efficacy of AV-203 in 25 xenograft models (expressed as percentage tumor growth inhibition (TGI)) and NRG1 RNA expression, as measured by quantitative RT-PCR, represented by the Ct value. The 25 data points are represented by (■). The linear regression is shown by a solid line, and the 95% confidence interval by dotted lines. Among 25 tumors tested, the Rho value was −0.601, with p=0.0015 (Spearman correlation).

As used herein, "AV-203" means the humanized anti-human ERBB3 monoclonal antibody whose full-length heavy chain amino acid sequence is SEQ ID NO: 9, and whose full-length light chain amino acid sequence is SEQ ID NO: 10.

As used herein, "ERBB3" (also known as HER3) means the human protein encoded by the gene identified by Entrez Gene ID No. 2065, and allelic variants thereof.

As used herein, "ERBB3 inhibitor" means a molecule (small molecule or macromolecule, e.g., an antibody or antigen binding fragment thereof) that binds to ERBB3 and inhibits, neutralizes, prevents or eliminates the biological activity of ERBB3 in a tumor cell.

As used herein, "NRG1" (also known as neuregulin-1, heregulin, HRG and HRG1) means the human protein encoded by the gene identified by Entrez Gene ID No. 3084, and allelic variants thereof.

As used herein, "optimum threshold score" means the threshold score at which the classifier gives the most desirable balance between the cost of false negative calls and false positive calls.

As used herein, "receiver operating characteristic" (ROC) curve means a plot of false positive rate (sensitivity) versus true positive rate (specificity) for a binary classifier system. In construction of an ROC curve, the following definitions apply:

False negative rate: FNR=1−TPR
True positive rate: TPR=true positive/(true positive+false negative)
False positive rate: FPR=false positive/(false positive+ true negative)

As used herein, "response" or "responding" to treatment means, with regard to a treated tumor, that the tumor displays: (a) slowing of growth, (b) cessation of growth, or (c) regression.

As used herein, a "NRG1 score" is a numerical value representing the level of NRG1 expression in a tumor. The NRG1 score can be based on NRG1 gene expression at the RNA level or at the protein level. For example, an NRG1 score could be expressed as a (1) Ct value from a qRT-PCR assay, or (2) staining intensity in an IHC assay. Ct value and NRG1 expression are inversely related. Therefore, a lower Ct value translates to a higher NRG1 score. The NRG1 score can be interpreted with respect to a threshold score, which can be empirically determined in a threshold determination analysis, e.g., using ROC curve analysis.

As used herein, "threshold determination analysis" means analysis of a dataset representing a given tumor type, e.g., human renal cell carcinoma, to determine a threshold score for that particular tumor type. The dataset representing a given tumor type includes, for each tumor from a population of such tumors: (a) actual tumor response data (response and non-response to an ERBB3 inhibitor such as an anti-ERBB3 antibody), and (b) NRG1 expression level.

As used herein, "threshold score" means a score above which a tumor is classified as being sensitive to treatment with an ERBB3 inhibitor.

ERBB3 Antibodies

The methods disclosed herein can be used for predicting tumor response to treatment with an ERBB3 inhibitor such as an anti-ERBB3 antibody, or antigen-binding fragment of an anti-ERBB3 antibody. In some embodiments, a tumor is classified as sensitive or resistant to an ERBB3 antibody (or antigen binding fragment thereof) that inhibits or prevents NRG1 (e.g., NRG1-β1) from binding to ERBB3, thereby indirectly inhibiting or preventing ligand-induced dimerization of ERBB3 (e.g., anti-ERBB3 antibodies AV-203, 04D01, 12A07, 18H02 and 22A02). In other embodiments, a tumor is classified as sensitive or resistant to an antibody (or antigen-binding fragment thereof) that inhibits or prevents ERBB3 dimerization, without preventing NRG1 binding to ERBB3 (e.g., anti-ERBB3 antibody 09D03 and 11G01).

In exemplary embodiments, the ERBB3 inhibitor is one of the following antibodies: AV-203, 04D01, 12A07, 18H02, 22A02, 11G01, and 09D03.

Anti-ERBB3 antibody AV-203 (originally designated as antibody 24C05) comprises an immunoglobulin heavy chain variable region comprising a $CDR_{H1}$ comprising an amino acid sequence selected from the group consisting of SEQ ID NO: 1, a $CDR_{H2}$ comprising the amino acid sequence of SEQ ID NO: 2, and a $CDR_{H3}$ comprising the amino acid sequence of SEQ ID NO: 3 as shown in FIG. 1; and an immunoglobulin light chain variable region comprising a $CDR_{L1}$ comprising the amino acid sequence of SEQ ID NO: 4, a $CDR_{L2}$ comprising the amino acid sequence of SEQ ID NO: 5, and a $CDR_{L3}$ comprising the amino acid sequence of SEQ ID NO: 6 as shown in FIG. 3. In an exemplary embodiment, antibody AV-203 comprises an immunoglobulin heavy chain variable region comprising the amino acid sequence of SEQ ID NO: 7 as shown in FIG. 2, and an immunoglobulin light chain variable region comprising the amino acid sequence of SEQ ID NO: 8 as shown in FIG. 4. In another exemplary embodiment, antibody AV-203 comprises an immunoglobulin heavy chain amino acid sequence of SEQ ID NO: 9 and an immunoglobulin light chain amino acid sequence of SEQ ID NO: 10, as shown in FIG. 5.

Anti-ERBB3 antibody 04D01 comprises an immunoglobulin heavy chain variable region comprising a $CDR_{H1}$ comprising the amino acid sequence of SEQ ID NO: 11, a $CDR_{H2}$ comprising the amino acid sequence of SEQ ID NO: 12, and a $CDR_{H3}$ comprising the amino acid sequence of SEQ ID NO: 13 as shown in FIG. 1; and an immunoglobulin light chain variable region comprising a $CDR_{L1}$ comprising the s amino acid sequence of SEQ ID NO: 14, a $CDR_{L2}$ comprising the amino acid sequence of SEQ ID NO: 15, and a $CDR_{L3}$ comprising the amino acid sequence of SEQ ID NO: 16 as shown in FIG. 3. In an exemplary embodiment, antibody 04D01 comprises an immunoglobulin heavy chain variable region comprising the amino acid sequence of SEQ ID NO: 17 as shown in FIG. 2, and an immunoglobulin light chain variable region comprising the amino acid sequence of SEQ ID NO: 18 as shown in FIG. 4. In another exemplary embodiment, antibody 04D01 comprises an immunoglobulin heavy chain amino acid sequence of SEQ ID NO: 19 and an immunoglobulin light chain amino acid sequence of SEQ ID NO: 20, as shown in FIG. 6.

Anti-ERBB3 antibody 09D03 comprises an immunoglobulin heavy chain variable region comprising a $CDR_{H1}$ comprising the amino acid sequence of SEQ ID NO: 21, a $CDR_{H2}$ comprising the amino acid sequence of SEQ ID NO: 22, and a $CDR_{H3}$ comprising the amino acid sequence of SEQ ID NO: 23 as shown in FIG. 1; and an immunoglobulin light chain variable region comprising a $CDR_{L1}$ comprising the amino acid sequence of SEQ ID NO: 24, a $CDR_{L2}$ comprising the amino acid sequence of SEQ ID NO: 25, and a $CDR_{L3}$ comprising the amino acid sequence of SEQ ID NO: 26 as shown in FIG. 3. In an exemplary embodiment, antibody 09D03 comprises an immunoglobulin heavy chain variable region comprising the amino acid sequence of SEQ ID NO: 27 as shown in FIG. 2, and immunoglobulin light chain variable region comprising the amino acid sequence of SEQ ID NO: 28 as shown in FIG. 4. In another exemplary embodiment, antibody 09D03 comprises an immunoglobulin heavy chain amino acid sequence of SEQ ID NO: 29 and an immunoglobulin light chain amino acid sequence of SEQ ID NO: 30, as shown in FIG. 7.

Anti-ERBB3 antibody 11G01 comprises an immunoglobulin heavy chain variable region comprising a $CDR_{H1}$ comprising the s amino acid sequence of SEQ ID NO: 31, a $CDR_{H2}$ comprising the amino acid sequence of SEQ ID NO: 32, and a $CDR_{H3}$ comprising the amino acid sequence of SEQ ID NO: 33 as shown in FIG. 1; and an immunoglobulin light chain variable region comprising a $CDR_{L1}$ comprising the amino acid sequence of SEQ ID NO: 34, a $CDR_{L2}$ comprising the amino acid sequence of SEQ ID NO: 15, and a $CDR_{L3}$ comprising the amino acid sequence of SEQ ID NO: 35 as shown in FIG. 3. In an exemplary embodiment, antibody 11G01 comprises an immunoglobulin heavy chain variable region comprising the amino acid sequence of SEQ ID NO: 36 as shown in FIG. 2, and an immunoglobulin light chain variable region comprising the amino acid sequence of SEQ ID NO: 37 as shown in FIG. 4. In another exemplary embodiment, antibody 11G01 comprises an immunoglobulin heavy chain amino acid sequence of SEQ ID NO: 38 and an immunoglobulin light chain amino acid sequence of SEQ ID NO: 39, as shown in FIG. 8.

Anti-ERBB3 antibody 12A07 comprises an immunoglobulin heavy chain variable region comprising a $CDR_{H1}$ comprising the amino acid sequence of SEQ ID NO: 40, a $CDR_{H2}$ comprising the amino acid sequence of SEQ ID NO: 41, and a $CDR_{H3}$ comprising the amino acid sequence of SEQ ID NO: 42 as shown in FIG. 1; and an immunoglobulin light chain variable region comprising a $CDR_{L1}$ comprising the amino acid sequence of SEQ ID NO: 14, a $CDR_{L2}$ comprising the amino acid sequence of SEQ ID NO: 15, and a $CDR_{L3}$ comprising the amino acid sequence of SEQ ID NO: 16 as shown in FIG. 3. In an exemplary embodiment, antibody 12A07 comprises an immunoglobulin heavy chain variable region comprising the amino acid sequence of SEQ ID NO: 43 as shown in FIG. 2, and an immunoglobulin light chain variable region comprising the amino acid sequence of SEQ ID NO: 44 as shown in FIG. 4. In another exemplary embodiment, antibody 12A07 comprises an immunoglobulin heavy chain amino acid sequence of SEQ ID NO: 45 and an immunoglobulin light chain amino acid sequence of SEQ ID NO: 46, as shown in FIG. 9.

Anti-ERBB3 antibody 18H02 comprises an immunoglobulin heavy chain variable region comprising a $CDR_{H1}$ comprising the amino acid sequence of SEQ ID NO: 47, a $CDR_{H2}$ comprising the amino acid sequence of SEQ ID NO: 48, and a $CDR_{H3}$ comprising the amino acid sequence of SEQ ID NO: 49 as shown in FIG. 1; and an immunoglobulin light chain variable region comprising a $CDR_{L1}$ comprising the amino acid sequence of SEQ ID NO: 50, a $CDR_{L2}$ comprising the amino acid sequence of SEQ ID NO: 51, and a $CDR_{L3}$ comprising the amino acid sequence of SEQ ID NO: 52 as shown in FIG. 3. In an exemplary embodiment, antibody 18H02 comprises an immunoglobulin heavy chain variable region comprising the amino acid sequence of SEQ ID NO: 53 as shown in FIG. 2, and an immunoglobulin light chain variable region comprising the amino acid sequence of SEQ ID NO: 54 as shown in FIG. 4. In another exemplary embodiment, antibody 18H02 comprises an immunoglobulin heavy chain amino acid sequence of SEQ ID NO: 55 and an immunoglobulin light chain amino acid sequence of SEQ ID NO: 56, as shown in FIG. 10.

Anti-ERBB3 antibody 22A02 comprises an immunoglobulin heavy chain variable region comprising a $CDR_{H1}$ comprising the amino acid sequence of SEQ ID NO: 57, a $CDR_{H2}$ comprising the amino acid sequence of SEQ ID NO: 58, and a $CDR_{H3}$ comprising the amino acid sequence of SEQ ID NO: 42 as shown in FIG. 1; and an immunoglobulin light chain variable region comprising a $CDR_{L1}$ comprising the amino acid sequence of SEQ ID NO: 14, a $CDR_{L2}$ comprising the amino acid sequence of SEQ ID NO: 15, and a $CDR_{L3}$ comprising the amino acid sequence of SEQ ID NO: 16 as shown in FIG. 3. In an exemplary embodiment, antibody 22A02 comprises an immunoglobulin heavy chain variable region comprising the amino acid sequence of SEQ ID NO: 59 as shown in FIG. 2, and an immunoglobulin light chain variable region comprising the amino acid sequence of SEQ ID NO: 60 as shown in FIG. 4. In another exemplary embodiment, antibody 22A02 comprises an immunoglobulin heavy chain amino acid sequence of SEQ ID NO: 61 and an immunoglobulin light chain amino acid sequence of SEQ ID NO: 62, as shown in FIG. 11.

It is contemplated that the skilled person would understand that a complete heavy or kappa chain antibody sequences can be created by ligating a variable region as described above to a respective constant region sequence(s) to produce active full length immunoglobulin heavy and light chains. For example, a complete heavy chain comprises a heavy variable sequence followed by the murine or human IgG1 or IgG2b heavy chain constant sequence (which are known in the art) and a complete kappa chain comprises a kappa variable sequence followed by the murine or human kappa light chain constant sequence (which are known in the art). It is further contemplated that CDR1, CDR2, and CDR3 sequences from the immunoglobulin heavy and light chains may be interposed between human or humanized immunoglobulin framework regions.

Tissue Sample

A tissue sample from a tumor in a human patient (e.g., a tissue sample from a tumor obtained from a human patient, e.g., a human patient being considered for treatment with an ERBB3 inhibitor) can be used as a source of RNA, a source of protein, or a source of thin sections for immunohistochemistry (IHC), so the level of NRG1 in the sample can be determined in practicing the disclosed methods. The tissue sample can be obtained by using conventional tumor biopsy instruments and procedures. Endoscopic biopsy, excisional biopsy, incisional biopsy, fine needle biopsy, punch biopsy, shave biopsy and skin biopsy are examples of recognized medical procedures that can be used by one of skill in the art to obtain tumor samples. The tumor tissue sample should be large enough to provide sufficient RNA, protein, or thin sections for measuring NRG1 and ERBB3 gene expression.

The tumor tissue sample can be in any form that allows measurement of NRG1 and ERBB3 expression or content.

In other words, the tissue sample must be sufficient for RNA extraction, protein extraction, or preparation of thin sections. Accordingly, the tissue sample can be fresh, preserved through suitable cryogenic techniques, or preserved through non-cryogenic techniques. A standard process for handling clinical biopsy specimens is to fix the tissue sample in formalin and then embed it in paraffin. Samples in this form are commonly known as formalin-fixed, paraffin-embedded (FFPE) tissue. Suitable techniques of tissue preparation for subsequent analysis are well-known to those of skill in the art.

NRG1 Gene Expression

As described herein, determining or measuring the level of NRG1 gene expression in a tissue sample from a tumor can be performed by any suitable method. Several such methods are known in the art. For example, determining NRG1 gene expression can be done by measuring the level or amount of NRG1 protein, or measuring the level or amount of NRG1 RNA, in a sample.

Neuregulin 1 is produced in numerous isoforms upon expression of the NRG1 gene. Relative abundance of the various isoforms appears to vary, depending on factors such as tissue type and/or developmental stage. The EGF-like domain of Neuregulin 1 is essential for binding to ERBB3. It is found in all of the various NRG1 isoforms as a beta variant (NRG1β) or alpha variant (NRG1α). Therefore, when determining the level NRG1 gene expression as described herein, the NRG1 assay preferably is designed to detect at least the EGF-like domain of NRG1, in order to detect most, if not all, of the NRG1 isoforms present. Accordingly, in some embodiments, PCR primers are designed to amplify a portion of the EGF-like domain. Similarly, in some embodiments, microarray probes are designed to hybridize with a sequence in the EGF-like domain or a sequence conserved across multiple variants. If an anti-NRG1 antibody is used to detect NRG1 protein, the antibody preferably will recognize the EGF-like domain.

In some embodiments, classification of a tumor as sensitive or resistant to treatment with an ERBB3 inhibitor is based solely on the expression of NRG1 in a tissue sample from the tumor. In other embodiments, expression of one or more other genes is measured in addition to NRG1 expression, to classify a tumor as sensitive or resistant to treatment with an ERBB3 inhibitor. It is contemplated herein that in embodiments when the expression of one or more other genes is measured in addition to NRG1, the one or more other genes do not include ErbB1, ErbB2, and ErbB3 (e.g., monomers, heterodimers and/or homodimers of any of ErbB1, ErbB2 and ErbB3, and/or phosphorylated ErbB1, ErbB2 and ErbB3 either in monomeric or dimeric form). In other embodiments, the expression of NRG1 is not measured in combination with beta-cellulin (BCT) secretion. It is further contemplated herein that the expression of one or more other genes measured in addition to NRG1 may include genes serving as controls or standards, e.g., for data normalization.

RNA Analysis

Conventional microarray analysis and quantitative polymerase chain reaction (PCR) are examples of methods for determining the level of NRG1 gene expression at the mRNA level. In some embodiments, RNA is extracted from the cells, tumor or tissue of interest using standard protocols. In other embodiments, RNA analysis is performed using techniques that do not require RNA isolation.

Methods for rapid and efficient extraction of eukaryotic mRNA, i.e., poly(a) RNA, from tissue samples are well established and known to those of skill in the art. See, e.g., Ausubel et al., 1997, *Current Protocols of Molecular Biology*, John Wiley & Sons. The tissue sample can be fresh, frozen or fixed paraffin-embedded (FFPE) samples such as clinical study tumor specimens. In general, RNA isolated from fresh or frozen tissue samples tends to be less fragmented than RNA from FFPE samples. FFPE samples of tumor material, however, are more readily available, and FFPE samples are suitable sources of RNA for use in methods of the present invention. For a discussion of FFPE samples as sources of RNA for gene expression profiling by RT-PCR, see, e.g., Clark-Langone et al., 2007, *BMC Genomics* 8:279. Also see, De Andres et al., 1995, *Biotechniques* 18:42044; and Baker et al., U.S. Patent Application Publication No. 2005/0095634. The use of commercially available kits with vendor's instructions for RNA extraction and preparation is widespread and common. Commercial vendors of various RNA isolation products and complete kits include Qiagen (Valencia, Calif.), Invitrogen (Carlsbad, Calif.), Ambion (Austin, Tex.) and Exiqon (Woburn, Mass.).

In general, RNA isolation begins with tissue/cell disruption. During tissue/cell disruption it is desirable to minimize RNA degradation by RNases. One approach to limiting RNase activity during the RNA isolation process is to ensure that a denaturant is in contact with cellular contents as soon as the cells are disrupted. Another common practice is to include one or more proteases in the RNA isolation process. Optionally, fresh tissue samples are immersed in an RNA stabilization solution, at room temperature, as soon as they are collected. The stabilization solution rapidly permeates the cells, stabilizing the RNA for storage at 4° C., for subsequent isolation. One such stabilization solution is available commercially as RNAlater®(Ambion, Austin, Tex.).

In some protocols, total RNA is isolated from disrupted tumor material by cesium chloride density gradient centrifugation. In general, mRNA makes up approximately 1% to 5% of total cellular RNA. Immobilized Oligo(dT), e.g., oligo(dT) cellulose, is commonly used to separate mRNA from ribosomal RNA and transfer RNA. If stored after isolation, RNA must be stored under RNase-free conditions. Methods for stable storage of isolated RNA are known in the art. Various commercial products for stable storage of RNA are available.

Microarray

The mRNA expression level of NRG1 can be measured using conventional DNA microarray expression profiling technology. A DNA microarray is a collection of specific DNA segments or probes affixed to a solid surface or substrate such as glass, plastic or silicon, with each specific DNA segment occupying a known location in the array. Hybridization with a sample of labeled RNA, usually under stringent hybridization conditions, allows detection and quantitation of RNA molecules corresponding to each probe in the array. After stringent washing to remove non-specifically bound sample material, the microarray is scanned by confocal laser microscopy or other suitable detection method. Modern commercial DNA microarrays, often known as DNA chips, typically contain tens of thousands of probes, and thus can measure expression of tens of thousands of genes simultaneously. Such microarrays can be used in practicing the present invention. Alternatively, custom chips containing as few probes as those needed to measure NRG1, plus necessary controls or standards, e.g., for data normalization, can be used in practicing the disclosed methods.

To facilitate data normalization, a two-color microarray reader can be used. In a two-color (two-channel) system, samples are labeled with a first fluorophore that emits at a first wavelength, while an RNA or cDNA standard is labeled with a second fluorophore that emits at a different wavelength. For example, Cy3 (570 nm) and Cy5 (670 nm) often are employed together in two-color microarray systems.

DNA microarray technology is well-developed, commercially available, and widely employed. Therefore, in performing disclosed methods, a person of ordinary skill in the art can use microarray technology to measure expression levels of genes encoding biomarker proteins without undue experimentation. DNA microarray chips, reagents (such as those for RNA or cDNA preparation, RNA or cDNA labeling, hybridization and washing solutions), instruments (such as microarray readers) and protocols are well known in the art and available from various commercial sources. Commercial vendors of microarray systems include Agilent Technologies (Santa Clara, Calif.) and Affymetrix (Santa Clara, Calif.), but other PCR systems can be used.

Quantitative PCR

The level of mRNA encoding NRG1 can be measured using conventional quantitative reverse transcriptase polymerase chain reaction (qRT-PCR) technology. Advantages of qRT-PCR include sensitivity, flexibility, quantitative accuracy, and ability to discriminate between closely related mRNAs. Guidance concerning the processing of tissue samples for quantitative PCR is available from various sources, including manufacturers and vendors of commercial instruments and reagents for qRT-PCR (e.g., Qiagen (Valencia, Calif.) and Ambion (Austin, Tex.)). Instruments and systems for automated performance of qRT-PCR are commercially available and used routinely in many laboratories. An example of a well-known commercial system is the Applied Biosystems 7900HT Fast Real-Time PCR System (Applied Biosystems, Foster City, Calif.).

Once mRNA is isolated, the first step in gene expression measurement by RT-PCR is the reverse transcription of the mRNA template into cDNA, which is then exponentially amplified in a PCR reaction. Two commonly used reverse transcriptases are avilo myeloblastosis virus reverse transcriptase (AMV-RT) and Moloney murine leukemia virus reverse transcriptase (MMLV-RT). The reverse transcription reaction typically is primed with specific primers, random hexamers, or oligo(dT) primers. Suitable primers are commercially available, e.g., GeneAmp® RNA PCR kit (Perkin Elmer, Waltham, Mass.). The resulting cDNA product can be used as a template in the subsequent polymerase chain reaction.

The PCR step is carried out using a thermostable DNA-dependent DNA polymerase. The polymerase most commonly used in PCR systems is a *Thermus aquaticus* (Taq) polymerase. The selectivity of PCR results from the use of primers that are complementary to the DNA region targeted for amplification, i.e., regions of the cDNAs reverse transcribed from genes encoding proteins of interest. Therefore, when qRT-PCR is employed in the present invention, primers specific to each marker gene are based on the cDNA sequence of the gene. Commercial technologies such as SYBR® green or TaqMan® (Applied Biosystems, Foster City, Calif.) can be used in accordance with the vendor's instructions. Messenger RNA levels can be normalized for differences in loading among samples by comparing the levels of housekeeping genes such as beta-actin or GAPDH. The level of mRNA expression can be expressed relative to any single control sample such as mRNA from normal, non-tumor tissue or cells. Alternatively, it can be expressed relative to mRNA from a pool of tumor samples, or tumor cell lines, or from a commercially available set of control mRNA.

Suitable primer sets for PCR analysis of expression of genes NRG1 or ERBB3 can be designed and synthesized by one of skill in the art, without undue experimentation. Alternatively, PCR primer sets for practicing the present invention can be purchased from commercial sources, e.g., Applied Biosystems. PCR primers preferably are about 17 to 25 nucleotides in length. Primers can be designed to have a particular melting temperature (Tm), using conventional algorithms for Tm estimation. Software for primer design and Tm estimation are available commercially, e.g., Primer Express™ (Applied Biosystems), and also are available on the internet, e.g., Primer3 (Massachusetts Institute of Technology). By applying established principles of PCR primer design, a large number of different primers can be used to measure the expression level of any given gene, including NRG1 and ERBB3.

qNPA™

In some embodiments, RNA analysis is performed using a technology that does not involve RNA extraction or isolation. One such technology is quantitative nuclease protection assay, which is commercially available under the name qNPA™ (High Throughput Genomics, Inc., Tucson, Ariz.). This technology can be advantageous when the tumor tissue samples to be analyzed are in the form of FFPE material. See, e.g., Roberts et al., 2007, *Laboratory Investigation* 87:979-997.

Protein Analysis

In other embodiments, NRG1 and ERBB3 gene expression can be detected at the protein level. Examples of methods for measuring the level of NRG1 or ERBB3 gene expression at the protein level include enzyme linked immunosorbent assay (ELISA) and IHC analysis.

ELISA

Performing an NRG1 ELISA requires at least one antibody against NRG1, i.e., the detection antibody. NRG1 protein from a sample to be analyzed is immobilized on a solid support such as a polystyrene microtiter plate. This immobilization can be by non-specific binding, i.e., through adsorption to the surface. Alternatively, immobilization can be by specific binding, i.e., through binding of NRG1 from the sample by a capture antibody (anti-NRG1 antibody different from the detection antibody), in a "sandwich" ELISA. After the NRG1 is immobilized, the detection antibody is added, and the detection antibody forms a complex with the bound NRG1. The detection antibody is linked to an enzyme, either directly or indirectly, e.g., through a secondary antibody that specifically recognizes the detection antibody. Typically between each step, the plate, with bound NRG1, is washed with a mild detergent solution. Typical ELISA protocols also include one or more blocking steps, which involve use of a non-specifically-binding protein such as bovine serum albumin to block unwanted non-specific binding of protein reagents to the plate. After a final wash step, the plate is developed by addition of an appropriate enzyme substrate, to produce a visible signal, which indicates the quantity of NRG1 in the sample. The substrate can be, e.g., a chromogenic substrate or a fluorogenic substrate. ELISA methods, reagents and equipment are well-known in the art and commercially available.

Immunohistochemistry (IHC)

The presence and level of NRG1 in a tumor tissue sample, or clinical specimen, can be determined (e.g., visualized) by immunohistochemistry (IHC) or immunofluorescence (IF).

Because clinical specimens often are preserved as formalin fixed paraffin embedded (FFPE) blocks, IHC and IF are particularly useful for measuring NRG1 protein in clinical specimens. Assaying NRG1 by IHC or IF requires at least one antibody against NRG1. Anti-NRG1 antibodies suitable for IHC and IF are commercially available. For example, suitable antibodies can be purchased from R&D Systems (Minneapolis, Minn.), abcam (Cambridge, Mass.), Santa Cruz Biotechnology, Inc. (Santa Cruz, Calif.), or Novus Biologicals (Littleton, Colo.). Using standard techniques, the anti-NRG1 antibody can be used to detect the presence of NRG1 protein in thin sections, e.g., 5 micron sections, obtained from tumors, including FFPE sections and frozen tumor sections. Typically, the tumor sections are initially treated in such a way as to retrieve the antigenic structure of proteins that were fixed in the initial process of collecting and preserving the tumor material. Slides are then blocked to prevent non-specific binding by the anti-NRG1 detection antibody. The presence of NRG1 protein is then detected by binding of the anti-NRG1 antibody (primary antibody) to the NRG1 protein. The detection antibody (secondary antibody), which recognizes and binds to the primary antibody, is linked to a detectable enzyme or fluorophore. Typically, the tumor sections are washed and blocked with non-specific protein such as bovine serum albumin between steps. If the detection antibody is linked to a detectable enzyme, the slide is developed using an appropriate enzyme substrate to produce a visible signal. If the detection antibody is linked to a fluorophore, the slide is viewed by using a fluorescence microscope. The samples can be counterstained with hematoxylin.

Data Interpretation

An NRG1 score for a tumor can be interpreted with respect to a threshold score. An NRG1 score that is equal to or higher than the threshold score can be interpreted as predictive of the tumor being sensitive (responsive) to treatment with an ERBB3 inhibitor, e.g., an ERBB3 antibody. Alternatively, NRG1 scores equal to or lower than the threshold score can be interpreted as predictive of a tumor being resistant (non-responsive) to treatment with an ERBB3 inhibitor.

An optimum threshold NRG1 score can be determined (or at least approximated) empirically by performing a threshold determination analysis. Preferably, threshold determination analysis includes receiver operator characteristic (ROC) curve analysis. ROC curve analysis is an established statistical technique, the application of which is within ordinary skill in the art. For a discussion of ROC curve analysis, see generally Zweig et al., 1993, "Receiver operating characteristic (ROC) plots: a fundamental evaluation tool in clinical medicine," *Clin. Chem.* 39:561-577; and Pepe, 2003, *The statistical evaluation of medical tests for classification and prediction*, Oxford Press, New York.

NRG1 scores and the optimum threshold NRG1 score may vary from tumor type to tumor type. Therefore, a threshold determination analysis preferably is performed on one or more datasets representing any given tumor type to be tested using the present invention. The dataset used for threshold determination analysis includes: (a) actual response data (response or non-response), and (b) an NRG1 score for each tumor sample from a group of tumors. Once an NRG1 score threshold is determined with respect to a given tumor type, that threshold can be applied to interpret NRG1 scores from tumors of that tumor type. In certain embodiments, a threshold score is determined by measuring NRG1 expression in tissue samples of tumors obtained from human patients previously treated with an anti-ERBB3 inhibitor and shown to be sensitive to the anti-ERBB3 inhibitor and human patients previously treated with an anti-ERBB3 inhibitor and shown to be resistant to anti-ERBB3 inhibitor.

The ROC curve analysis can be performed as follows. Any sample with an NRG1 score greater than or equal to the threshold is identified as a responder (sensitive). Alternatively, any sample with an NRG1 score less than the threshold is identified as a non-responder (resistant). For every NRG1 score from a tested set of samples, "responders" and "non-responders" (hypothetical calls) are classified using that score as the threshold. This process enables calculation of TPR (y vector) and FPR (x vector) for each potential threshold, through comparison of hypothetical calls against the actual response data for the data set. Then an ROC curve is constructed by making a dot plot, using the TPR vector, and FPR vector. If the ROC curve is above the diagonal from (0, 0) point to (1.0, 0.5) point, it shows that the NRG1 test result is a better test result than random.

The ROC curve can be used to identify the best operating point, or optimum threshold. The best operating point is the one that yields the best balance between the cost of false positives weighed against the cost of false negatives. These costs need not be equal. The average expected cost (C) of classification at point x,y in the ROC space is determined by the following formula.

$$C=(1-p)\text{alpha}*x+p*\text{beta}(1-y)$$

wherein:
alpha=cost of a false positive,
beta=cost of missing a positive (false negative), and
p=proportion of positive cases.

False positives and false negatives can be weighted differently by assigning different values for alpha and beta. For example, if it is decided to include more patients in the responder group at the cost of treating more patients who are non-responders, one can put more weight on alpha. In this case, it is assumed that the cost of false positive and false negative is the same (alpha equals to beta). Therefore, the average expected cost of classification at point x,y in the ROC space is:

$$C'=(1-p)*x+p*(1-y).$$

The smallest C' can be calculated after using all pairs of false positive and false negative (x, y). The optimum score threshold is calculated as the score of the (x, y) at C'.

In addition to predicting whether a tumor will be sensitive or resistant to treatment with an ERBB3 inhibitor, i.e., binary classification, an NRG1 score provides an approximate, but useful, indication of how likely a tumor is to be sensitive or resistant. In general, the higher the NRG1 score, the more likely a tumor is to be sensitive to an ERBB3 inhibitor, and the lower the NRG1 score, the more likely a tumor is to be resistant to an ERBB3 inhibitor.

Test Kits

Also disclosed is a diagnostic test kit comprising certain components for performing methods of the invention. A diagnostic test kit enhances convenience, speed and reproducibility in the performance of diagnostic assays. For example, in an exemplary qRT-PCR-based embodiment, a basic diagnostic test kit includes PCR primers for analyzing expression of NRG1. In other embodiments, a more elaborate test kit contains not only PCR primers, but also buffers, reagents and detailed instructions for measuring NRG1 expression levels, using PCR technology. In some embodiments, the kit includes a test protocol and all the consumable components needed for the test, except the RNA sample(s).

In an exemplary DNA microarray-based embodiment, a test kit includes a micro fluidic card (array) designed for use with a particular instrument. Optionally, the micro fluidic card is a custom made device designed specifically for measurement of NRG1. Such custom micro fluidic cards are commercially available. For example, the TaqMan Array is a 384-well micro fluidic card (array) designed for use with the Applied Biosystems 7900HT Fast Real Time PCR System (Applied Biosystems, Foster City, Calif.). It is understood that additional probes can optionally be included on a fluidic card to measure the expression of one or more additional genes. Such additional genes may be included to serve as controls or standards, e.g., for data normalization, or may be otherwise informative.

In some embodiments, the test kit contains materials for determining NRG1 content by IHC. An IHC kit, for example, may contain a primary antibody against NRG1, and a secondary antibody conjugated to a reporter enzyme, e.g., horseradish peroxidase. In some embodiments, the secondary antibody is replaced with a conjugated polymer that specifically recognizes the primary antibody.

TABLE 1

Summary of Data from Xenograft Studies

| Xenograft Model | Cancer Type | TGI (%) | hNRG1 Ct | hERBB3 Ct |
|---|---|---|---|---|
| HCC2429 | Lung | −10.0 | 23.8 | 23.4 |
| H23 | Lung | −3.8 | 24.2 | 24.5 |
| AN3CA | Endometrial | 0.0 | 27.6 | 22.8 |
| LS1034 | Colorectal | 0.0 | 32.4 | 18.6 |
| MFM-223 | Breast | 0.0 | 35.5 | 19.7 |
| MFE-296 | Endometrial | 5.0 | 32.3 | 23.8 |
| H716 | Colorectal | 11.0 | 34.0 | 21.4 |
| H441 | Lung | 11.1 | 31.7 | 20.9 |
| SW1990 | Pancreas | 29 | 18.6 | 21.4 |
| HCC827 | Lung | 32.0 | 36.0 | 21.5 |
| Snu16 | Gastric | 35.0 | 31.8 | 20.5 |
| LOVO | Colorectal | 49.0 | 28.6 | 18.4 |
| H1048 | Lung | 53.0 | 26.0 | 20.8 |
| H1993 | Lung | 56.6 | 24.4 | 22.6 |
| A431 | Skin | 58.0 | 21.2 | 21.6 |
| H322 | Lung | 62.6 | 22.4 | 21.2 |
| CAPAN-1 | Pancreas | 66.0 | 24.2 | 19.2 |
| A498 | Kidney | 68.3 | 22.9 | 21.3 |
| H522 | Lung | 68.6 | 17.5 | 24.2 |
| Calu-3 | Lung | 69.0 | 20.8 | 19.4 |
| A549 | Lung | 74.0 | 20.6 | 20.3 |
| BxPC3 | Pancreas | 76.5 | 20.1 | 19.3 |
| MDA-MB-453 | Breast | 85.3 | 30.8 | 18.5 |
| H358 | Lung | 89.0 | 22.2 | 27.3 |
| HCC95 | Lung | 95.0 | 17.7 | 22.2 |

EXAMPLES

The invention is further illustrated by the following examples. The examples are provided for illustrative purposes only, and are not to be construed as limiting the scope or content of the invention in any way.

Example 1: Xenograft Tumor Response to AV-203

Evaluation of tumor response to AV-203 was performed as follows. In order to establish xenograft tumor, tumor cells were initially grown in culture at 37° C. in an atmosphere containing 5% CO2, using medium containing 10% fetal bovine serum. Cells were inoculated subcutaneously into the flank of 8-week old female NCR nude or CB.17 SCID mice (Taconic Labs) with 2–10×10$^6$ cells per mouse in 50% matrigel (BD Biosciences, Cat No. 356237). Tumor measurements were taken twice weekly using vernier calipers. Tumor volume was calculated using the formula: width× width×length/2. When tumors reached approximately 200 mm$^3$, the mice were randomized into two groups of 10 mice each, PBS vehicle control or AV-203 dosed intraperitoneally (IP) at 20 mg/kg twice weekly. In some studies, a second control group was used, which received human IgG dosed at 20 mg/kg IP twice weekly.

In total, 25 xenograft tumors were treated with AV-203. Response to AV-203 was varied, ranging from −10% tumor growth inhibition (TGI) to tumor regression. "Tumor regression" means that a tumor is smaller at the end of the evaluation period compared to the size of the tumor at the beginning of the evaluation period prior to treatment. Based on the tumor growth inhibition achieved, responders (defined as those with TGI >60%) and non-responders (defined as those with TGI <60%) were identified. Of the 25 tumors evaluated, 10 were found to be responders (e.g., a hNRG1 Ct value equal to or less than 22.9), and 15 were found to be non-responders (Table 1). These groups enabled the identification of a molecular marker for AV-203 responsiveness.

Example 2: Relationship Between AV-203 Response and NRG1 Levels

For the 25 tumors that were evaluated, RNA was prepared from an untreated healthy tumor. Flash frozen tumor samples were pulverized using Covaris CryoPrep™ system (Covaris Inc. Model CP-02). Approximately 30 mg of pulverized tumor material was transferred into a 2 mL SafeLock™ tube (Eppendorf, Cat. No. 02236652). One mL of TRIzol, (Invitrogen, Cat. No. 15596-026) and one (5 mm) stainless steel shaker bead (Qiagen, Cat. No. 69989) were added to each tube. The tubes were then placed in racks in the Tissue Lyser II™ (Qiagen, Cat. No. 85300) for cell lysis. The samples were shaken for two 30-second cycles. The racks then were rotated and shaken again for two more cycles.

The total RNA (aqueous phase) was extracted from the cell lysate by the addition of 200 μL chloroform to each sample. The samples were shaken vigorously for 15 seconds and centrifuged at 12,000 rpm for 15 minutes at 4° C. The upper supernatants (350 μL) were transferred to new 2 mL SafeLock™ tube and placed in QIAcube™ Automated Purification Instrument (Qiagen, Cat. No. 9001292) for automated RNA isolation with RNeasy™ Mini QIAcube Kit (Qiagen, Cat. No. 74116). A DNase I treatment step was included in the RNA isolation. The isolated total RNA concentration was measured with NanoDrop™ (Thermo Scientific, Model 1000), and the RNA integrity was determined by electrophoresis to verify the position of the 18S band and detection of any RNA degradation. The RNA was aliquoted into two 1.7 mL microtubes (Axygen Cat. No. MCT-175-C) and stored at −80° C.

Human NRG1, ERBB3 and β-Actin expression levels were determined using quantitative, real-time RT-PCR. Total tumor RNA expression was assayed using Quanti-Tect™ SYBR Green RT PCR Kit (Qiagen Cat. No. 204245) and run on a Applied Biosystems Thermocycler, Model 7900HT Fast Real-Time PCR System (Applied Biosystems, Cat. No. 4329001). Each RNA tumor sample was assayed in quadruplicate in 20 µL reactions. Each reaction contained 50 ng of total tumor RNA, 10 µL of 2× QuantiTect™ SYBR Green RT-PCR Master Mix, 0.2 µL QuantiTect RT Mix and forward and reverse gene specific primers (synthesized by Eurofins MWG Operon) at final concentration of 900 nM. The reactions setup using Qiagen BioRobot Rapidplate liquid handling system in a 384-well plate (Applied Biosystems, Cat. No. 4309849) and sealed with MicroAmp Optical Adhesive Film (Applied Biosystems, Cat. No. 4311971). The Real-Time plate was assayed with the following Program: 30 minutes at 50° C., 15 minutes at 95° C., followed by 40 cycles of 15 seconds at 95° C., 30 seconds at 54° C., 30 seconds at 72° C. Cycle threshold (Ct) value averages were then calculated in Microsoft Excel. Ct value is defined as cycle number at the threshold level of log-based fluorescence. A low Ct value reflects a high specific RNA level (i.e., a low Ct value reflects high expression of NRG1).

AV-203 tumor growth inhibition in these 25 tumors was then plotted against NRG1 expression levels (represented as Ct values) within each tumor. As shown in FIG. 12, a positive correlation was observed between tumor growth inhibition and NRG1 expression. More specifically, increased tumor growth inhibition after treatment with AV-203 correlated with increased NRG1 expression (lower Ct value). This correlation was found to be highly statistically significant (Table 2).

TABLE 2

Statistical Analysis of NRG1 Expression and AV-203 In Vivo Efficacy

| | |
|---|---|
| Number of XY Pairs | 25 |
| Spearman r | −0.601 |
| 95% confidence interval | −0.8093 to −0.2583 |
| P value (two-tailed) | 0.0015 |
| P value summary | ** |
| Exact or approximate P value? | Gaussian Approximation |
| Is the correlation significant? (alpha = 0.05) | Yes |

Example 3: Relationship Between AV-203 Response and ERBB3 Levels

Figure 13:
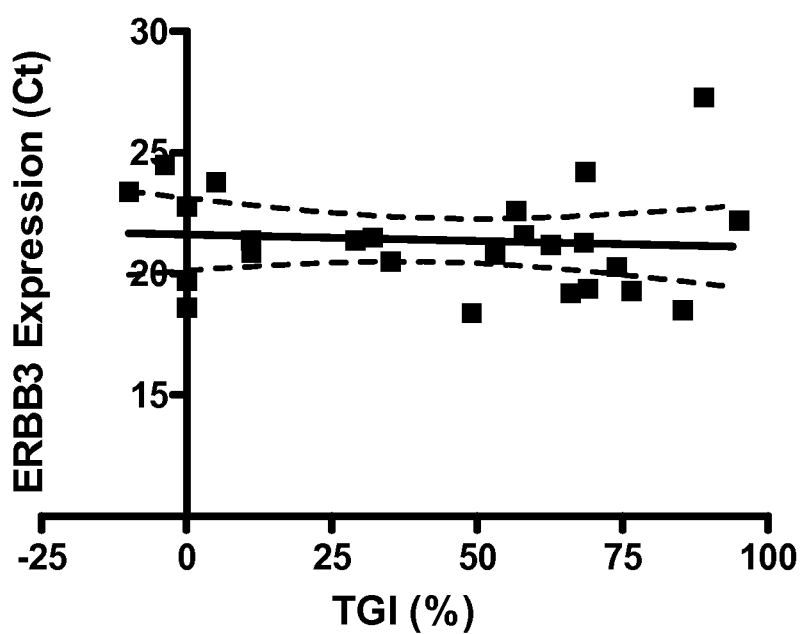
FIG. 13 is a scatter plot with a linear regression trend line showing the relationship between the in vivo efficacy of AV-203 in 25 xenograft models (expressed as percentage TGI) and ERBB3 RNA expression, as measured by quantitative RT-PCR, represented by the Ct value. The 25 data points are represented by (■). The linear regression is shown by a solid line, and the 95% confidence interval by dotted lines.

As described for NRG1, ERBB3 levels were also determined by quantitative RT-PCR from these 25 tumor models. AV-203 tumor growth inhibition in these 25 tumors was then plotted against ERBB3 expression levels (represented as Ct values) for each tumor. As shown in FIG. 13, tumor growth inhibition did not correlate with increased ERBB3 expression, even though ERBB3 is the target for AV-203.

Example 4: NRG1 Threshold Determination

Figure 14:
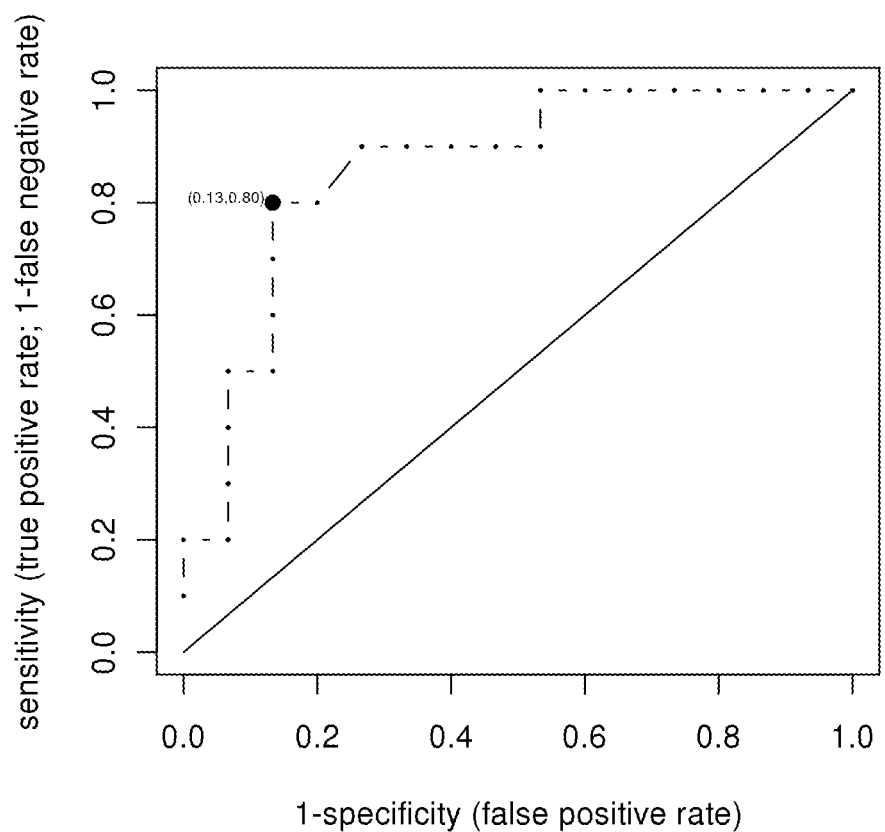
FIG. 14 is a Receiver operator characteristic (ROC) curve based on the data in FIG. 13, to determine the optimum threshold PGS score. This ROC curve indicates that the optimum threshold is Ct=22.9, which yields a false positive rate of 0.13, and a false negative rate of 0.2.
Figure 15:
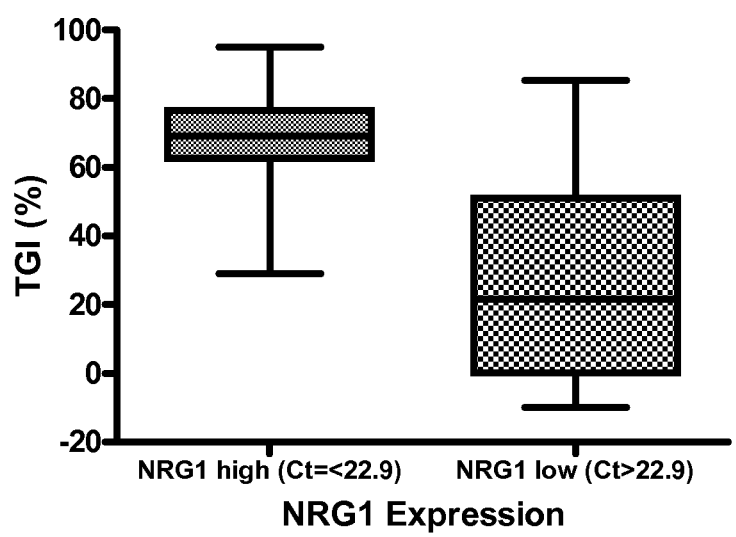
FIG. 15 is a box graph summarizing AV-203 in vivo efficacy in xenograft models separated by high NRG1-expressing tumors (Ct=<22.9) and low NRG1-expressing tumors (Ct>22.9).

Using the Ct values for NRG1 from the AV-203 responding (sensitive) and non-responding (resistant) xenograft tumor models, a receiver operator characteristic (ROC) curve was generated to determine an NRG1 expression threshold useful to predict AV-203 tumor response (FIG. 14). In general, a ROC curve is used to determine if the test result (e.g., an NRG1 biomarker test result) is significantly different from a random event and to determine the optimum threshold score (e.g., an optimum threshold NRG1 score). For example, if the test results are random, a diagonal line would divide the ROC space. In this example, the ROC curve is above the diagonal line indicating that the test is achieving a high degree of separation between responders and non-responders (FIG. 14). As shown in FIG. 14, the optimum threshold is Ct=22.9, which yields a false positive rate of 0.13, and a false negative rate of 0.2. Results of the ROC analysis indicate that AV-203 tumor response can be predicted by high NRG1 expression level, using a cut-off at Ct value 22.9. Using the xenograft tumor models listed in Table 1, the Ct value cut-off of 22.9 (e.g., equal to or less than 22.9) predicted AV-203 response with statistical significance (FIG. 15). As shown in FIG. 15, increased TGI was observed following treatment with AV-203 in tumors with a low Ct value (which indicates high NRG1 expression and a high NRG1 score).

Example 5: Primary Human Tumor Model Response

In order to validate this prediction method for response to AV-203, primary human tumor models were classified as having high or low NRG1 expression, based on a microarray analysis of the primary human tumors. These models were then tested for response to AV-203 treatment.

Evaluation of human primary tumor response to AV-203 was performed as follows. Primary human tumors were collected from surgical resection. Tumor samples were shipped on wet ice overnight in media containing 10% FBS. Upon arrival, tumor samples were cut into 2 mm×2 mm fragments and implanted subcutaneously into five NCR nude mice (Taconic) using a 10 gauge trocar needle. In order to establish xenograft tumor material to be used for efficacy studies, tumors were collected at 500 mm³ and propagated further into 20 sites. Once these tumors achieved a size of 500 mm³, they were collected for further propagation, efficacy studies, and molecular characterization. For efficacy studies, tumor fragments were implanted subcutaneously into 8-week old female NCR nude mice. Tumor measurements were taken twice weekly, using vernier calipers. Tumor volume was calculated using the formula: width× width×length/2. When tumors reached approximately 200 mm³, the mice were randomized into two groups of 10 mice each, PBS vehicle control, or AV-203 dosed intraperitoneally (IP) at 20 mg/kg twice weekly. In some studies, a second control group was used, which received human IgG dosed at 20 mg/kg twice weekly.

Figure 16:
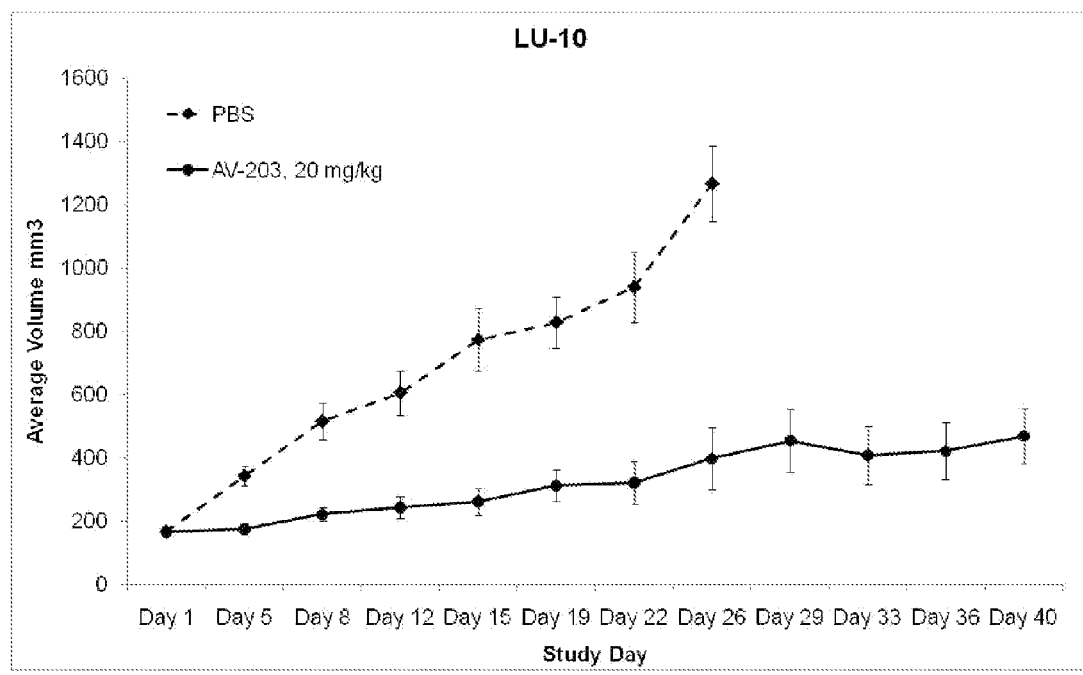
FIG. 16 is a graph summarizing efficacy data for PBS vehicle control (♦) and the anti-ERBB3 antibody AV-203 (●) against LU-10 human primary lung tumor xenografts dosed at 20 mg/kg in NCR nude mice.
Figure 17:
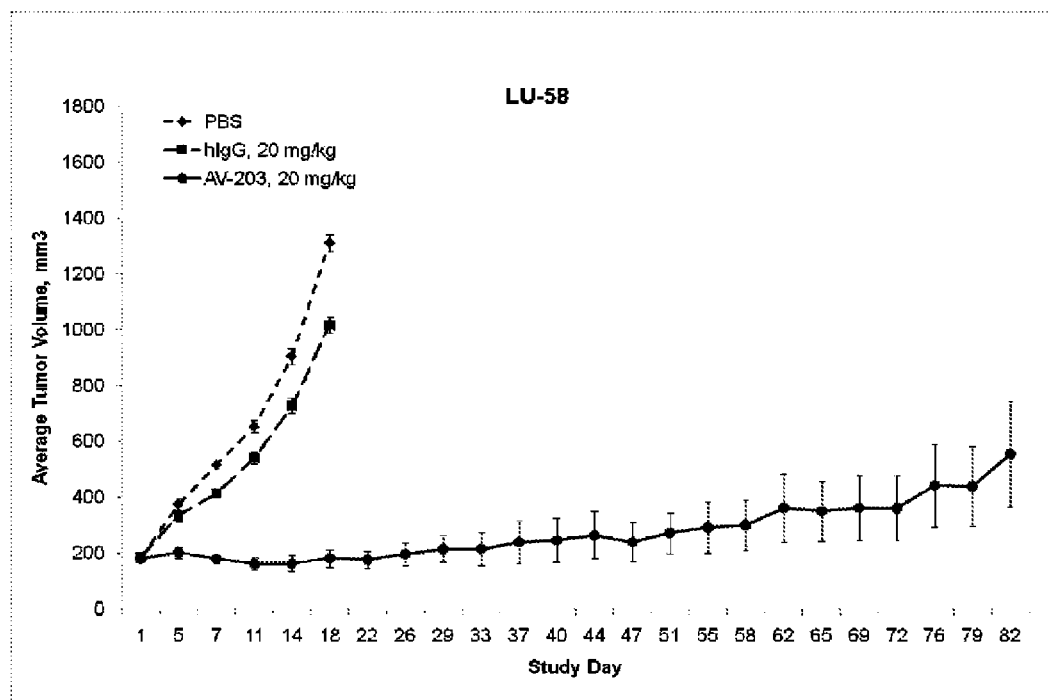
FIG. 17 is a graph summarizing efficacy data for PBS vehicle control (♦), human IgG control (■) and the anti-ERBB3 antibody AV-203 (●) against LU-58 human primary lung tumor xenografts dosed at 20 mg/kg in NCR nude mice.
Figure 18:
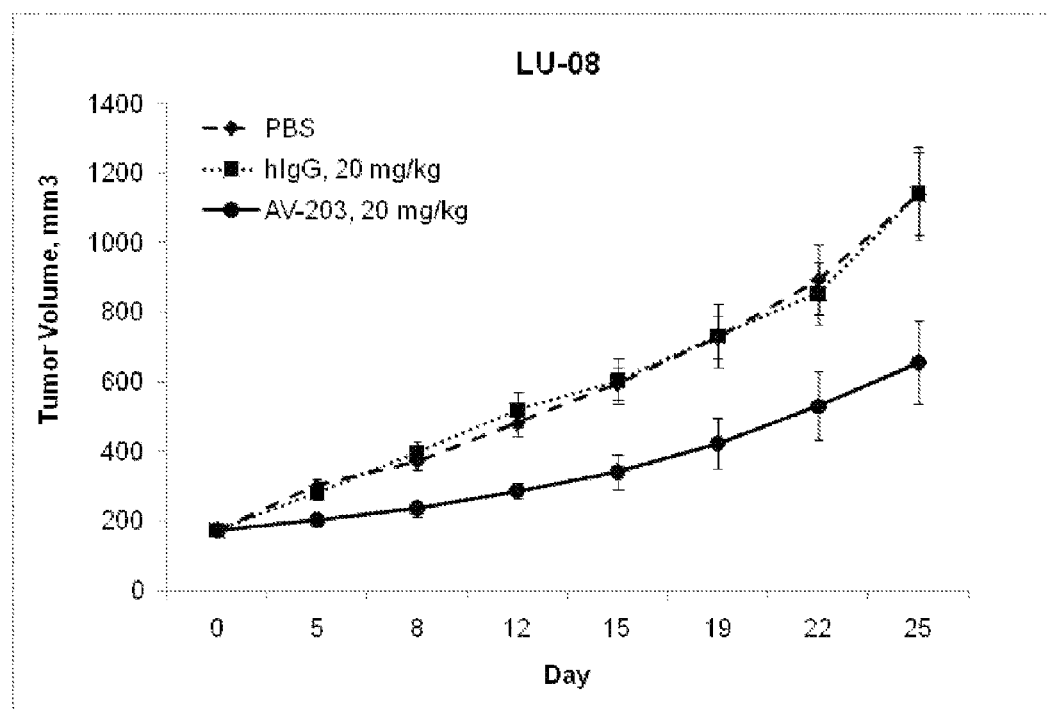
FIG. 18 is a graph summarizing efficacy data for PBS vehicle control (♦), human IgG control (■) and the anti-ERBB3 antibody AV-203 (●) against LU-08 human primary lung tumor xenografts dosed at 20 mg/kg in NCR nude mice.
Figure 19:
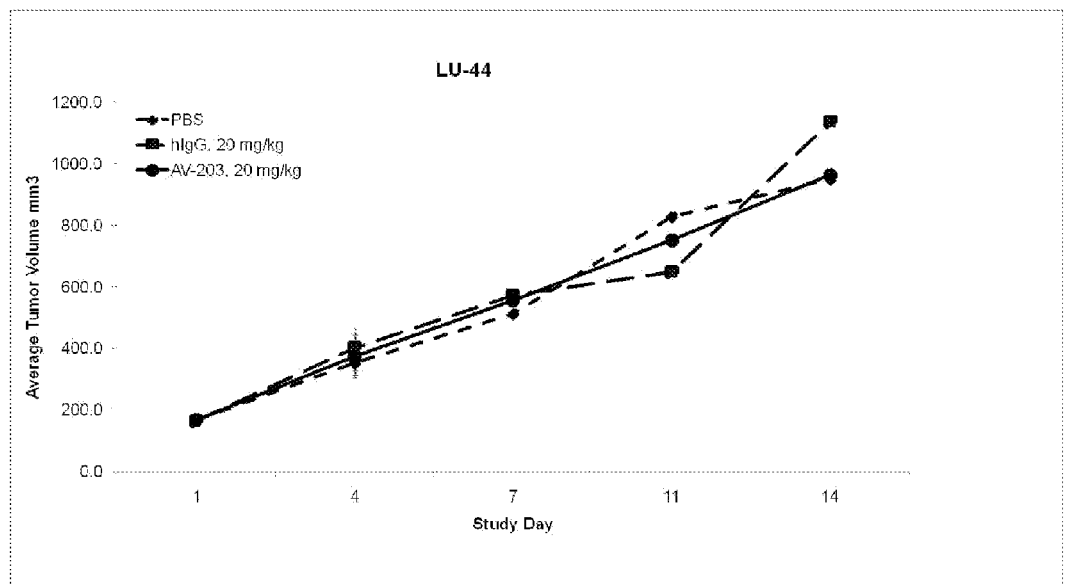
FIG. 19 is a graph summarizing efficacy data for PBS vehicle control (♦), human IgG control (■) and the anti-ERBB3 antibody AV-203 (●) against LU-44 human primary lung tumor xenografts dosed at 20 mg/kg in NCR nude mice.

In total, xenografts of four primary human lung tumors were treated with AV-203. Two were predicted to respond, and two were predicted not to respond, based on NRG1 expression ranking of the microarray data. The two NRG1 high human primary tumors that were predicted to respond to AV-203 treatment did respond, displaying significant tumor growth inhibition. Data from these sensitive tumors are summarized in FIGS. 16 and 17. The two NRG1 low human primary tumors predicted not to respond, did not respond to AV-203 treatment. Data from the resistant tumors are summarized in FIGS. 18 and 19. These data demonstrated that human primary tumor sensitivity to treatment with AV-203 can be predicted on the basis of high NRG1 expression in the tumor.

Example 6: Xenograft Tumor Model Response to Anti-ERBB3 Antibody AV-203

Figure 20:
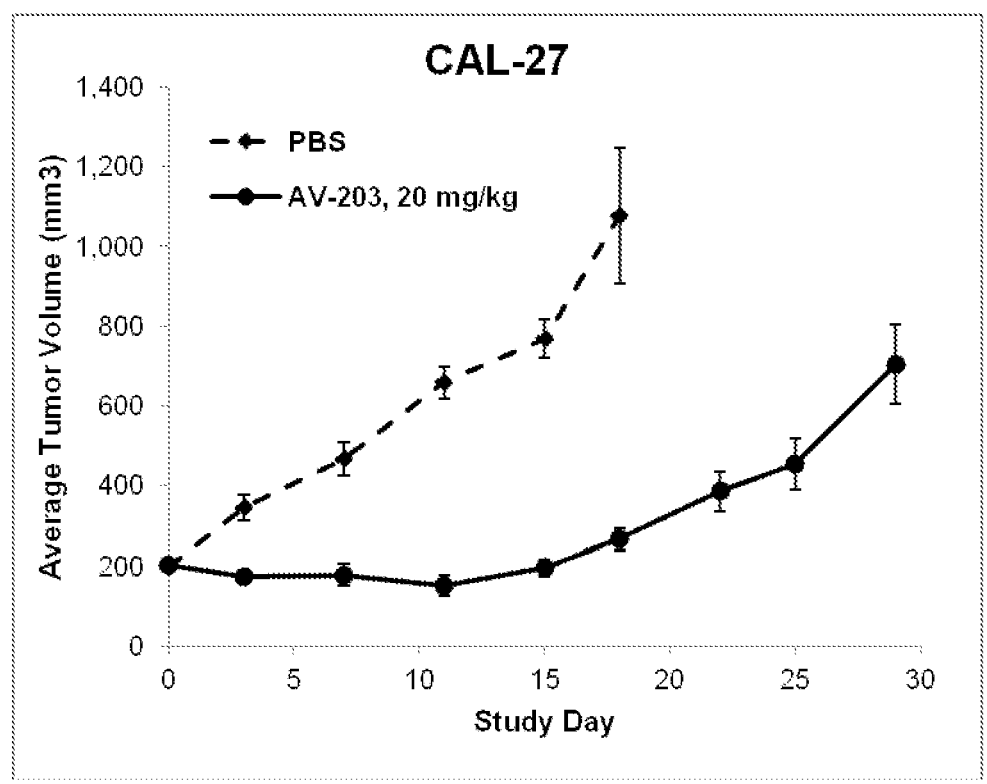
FIG. 20 is a graph summarizing efficacy data for PBS vehicle control (♦) and the anti-ERBB3 antibody AV-203 (●) against CAL-27 human head and neck cancer xenografts dosed at 20 mg/kg in CB17-SCID mice.
Figure 21:
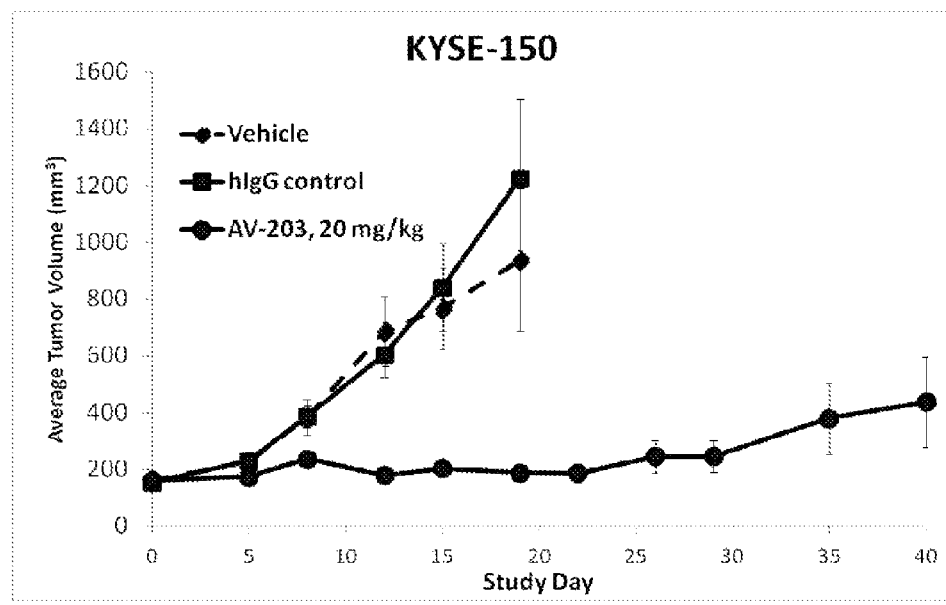
FIG. 21 is a graph summarizing efficacy data for PBS vehicle control (♦), human IgG control (■) and the anti-ERBB3 antibody AV-203 (●) against KYSE-150 human esophageal cancer xenografts dosed at 20 mg/kg in NCR nude mice
Figure 22:
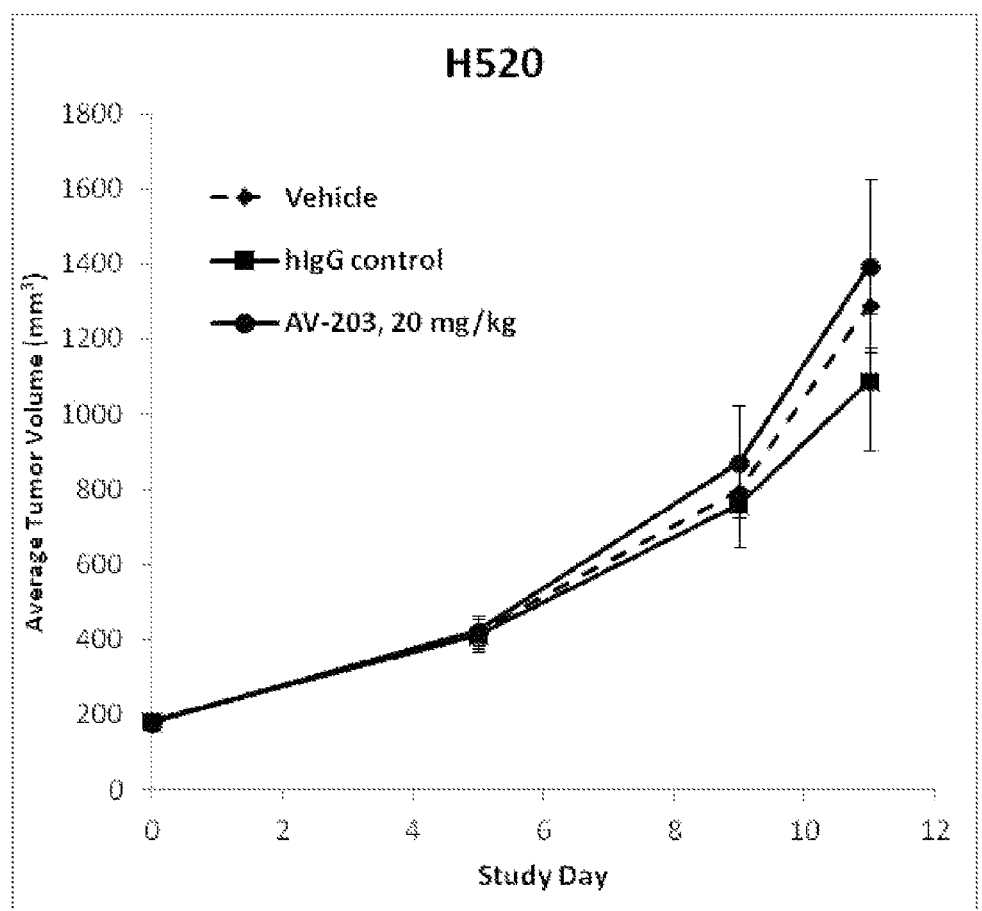
FIG. 22 is a graph summarizing efficacy data for PBS vehicle control (♦), human IgG control (■) and the anti-ERBB3 antibody AV-203 (●) against H520 human non-small cell lung carcinoma xenografts dosed at 20 mg/kg in NCR nude mice.

Two additional xenograft tumors (i.e., a CAL-27 head and neck tumor xenograft and a KYSE 150 esophageal tumor xenograft) were selected for high NRG1 expression based on the Ct value cut-off of 22.9 (e.g., equal to or less than 22.9) outlined in Example 4 and, therefore, were predicted to respond to AV-203. In addition, an H520 non-small cell lung carcinoma (NSCLC) xenograft tumor was selected for low NRG1 expression based on the same Ct value cut-off of 22.9 outlined in Example 4 and, therefore, was predicted not to respond to AV-203. All three tumor models were treated with 20 mg/kg of antibody AV-203. The response to antibody AV-203 ranged from 75.2-79.9% tumor growth inhibition for the sensitive tumors (i.e., CAL-27 and KYSE 150) (TGI, see Table 3 and FIGS. 20-21) and was −8.0% TGI for the resistant tumor (i.e., H520) (see Table 3 and FIG. 22).

TABLE 3

Summary Table of Xenograft Tumors Treated with Antibody AV-203

| Xenograft Model | Cancer Type | TGI (%) | hNRG1 Ct |
|---|---|---|---|
| CAL-27 | Head and Neck | 75.2 | 20.1 |
| KYSE 150 | Esophageal | 79.9 | 19.1 |
| H520 | NSCLC | −8.0 | 23.7 |

These data demonstrate that the response of solid tumors to treatment with AV-203 can be predicted by measuring NRG1 expression.

Example 7: Xenograft Tumor Model Response to Anti-ERBB3 Antibody 11G01

To validate the prediction method for response to other anti-ERBB3 antibodies, tumor models expressing high NRG1 levels were treated with an anti-ERBB3 antibody having a different mechanism of action from AV-203. As discussed above, AV-203 inhibits binding of NRG1 to ERBB3, therefore, the following experiment was conducted using an antibody that blocks dimerization of ERBB3 without inhibiting binding of NRG1 to ERBB3, i.e., antibody 11G01. Evaluation of tumor response to antibody 11G01 was performed as described in Example 1.

Figure 23:
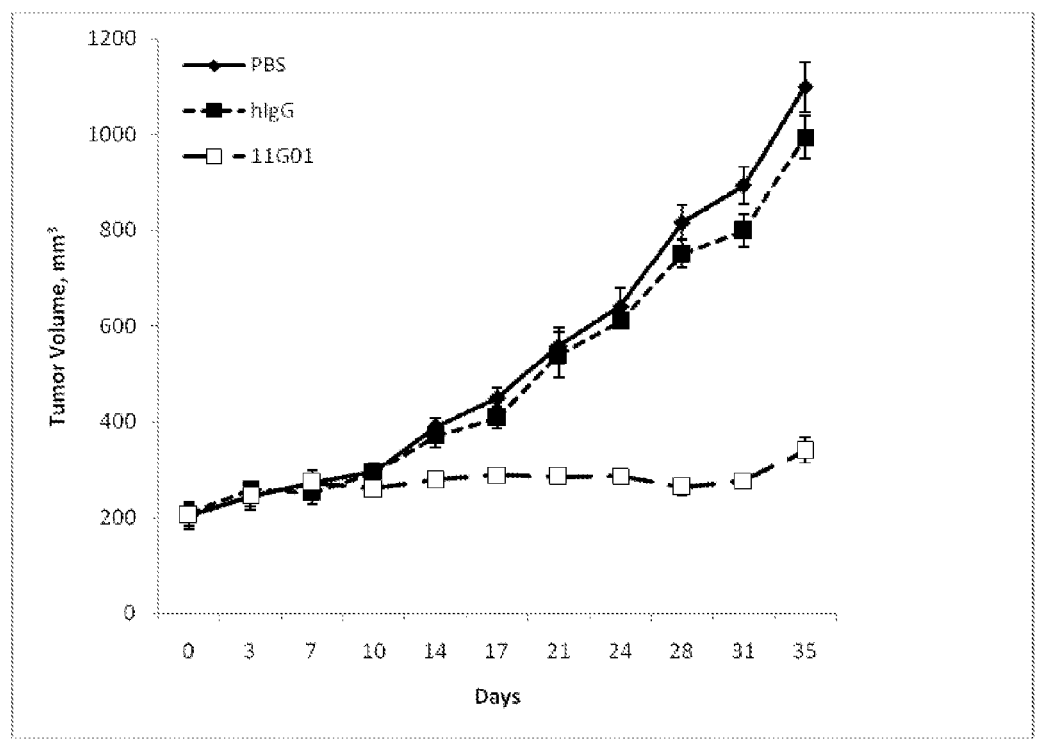
FIG. 23 is a graph summarizing efficacy data for PBS vehicle control (♦), human IgG control (■) and the anti- ERBB3 antibody 11G01 (□) against BxPC3 pancreatic tumor xenografts dosed at 20 mg/kg in CB.17 SCID mice.
Figure 24:
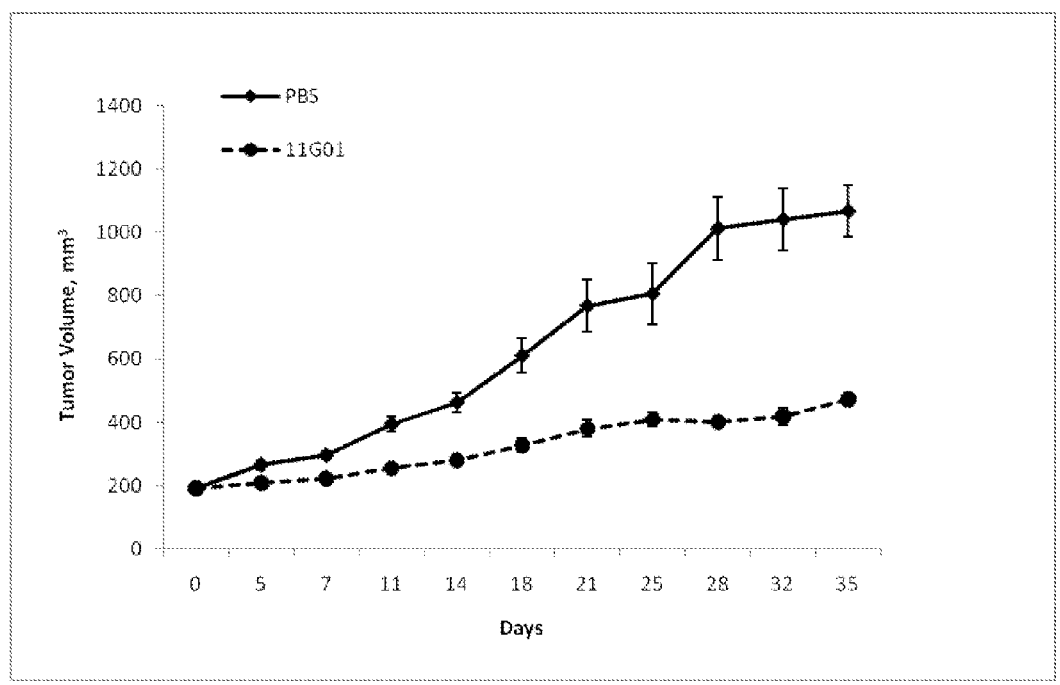
FIG. 24 is a graph summarizing efficacy data for PBS vehicle control (♦) and the anti-ERBB3 antibody 11G01 (●) against DU145 prostate tumor xenografts dosed at 20 mg/kg in CB.17 SCID mice.
Figure 25:
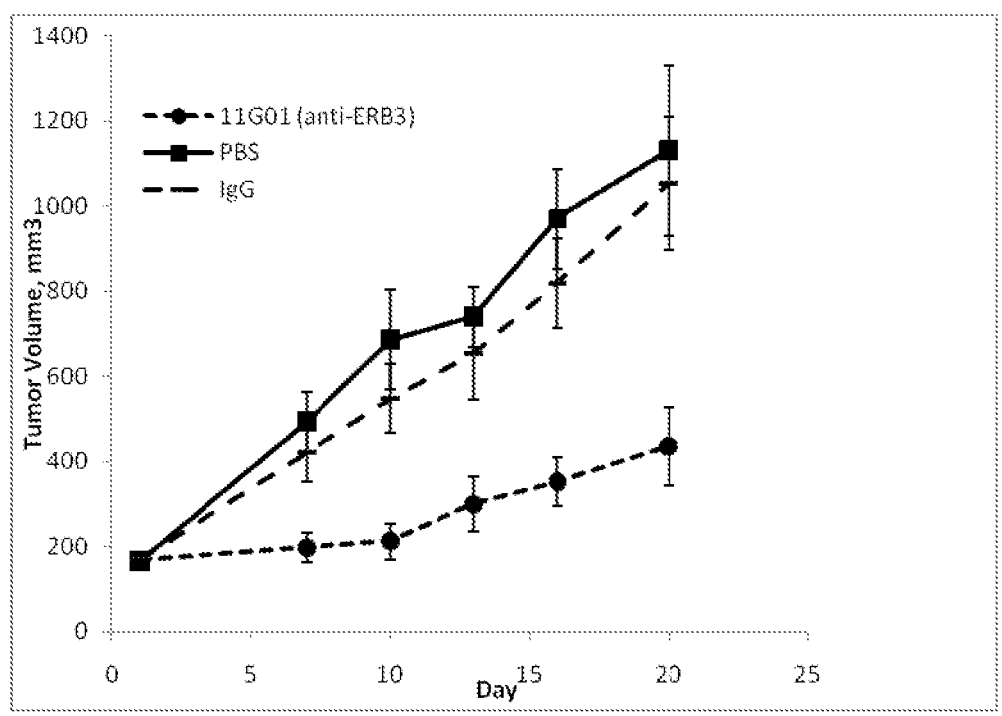
FIG. 25 is a graph summarizing efficacy data for PBS vehicle control (■), human IgG control (- - -) and the anti-ERBB3 antibody 11G01 (5θ) against H322 lung tumor xenografts dosed at 20 mg/kg in NCR nude mice.

Three xenograft tumors (i.e., a BxPC3 pancreas tumor xenograft, a DU145 prostate tumor xenograft and an H322 lung tumor xenograft) were selected for high NRG1 expression based on the Ct value cut-off of 22.9 (e.g., equal to or less than 22.9) outlined in Example 4 and, therefore, were predicted to respond to an anti-ERBB3 antibody. All 3 tumor models were treated with 20 mg/kg of antibody 11G01. Response to antibody 11G01 ranged from 60-72% tumor growth inhibition (TGI, see Table 4 and FIGS. 23-25).

TABLE 4

Summary Table of Xenograft Tumors Treated with Antibody 11G01

| Xenograft Model | Cancer Type | TGI (%) | hNRG1 Ct | hERBB3 Ct |
|---|---|---|---|---|
| BxPC3 | Pancreas | 71.8 | 20.1 | 19.3 |
| DU145 | Prostate | 60.0 | 22.3 | 19.6 |
| H322 | Lung | 61.5 | 22.4 | 21.2 |

Using the same cut-off of response as described in Examples 1 and 4 (i.e., an hNRG1 Ct value equal to or less than 22.9), all three tumors were considered as responding to antibody 11G01. These data demonstrate that the response of solid tumors to treatment with anti-ERBB3 antibodies including neutralizing antibodies (e.g., AV-203) and dimerization inhibiting antibodies (e.g., antibody 11G01) can be predicted by measuring high hNRG1 expression.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

What is claimed is:

1. A method of treating a tumor with an anti-ERBB3 antibody, the method comprising:
   administering the anti-ERBB3 antibody to a subject with a tumor likely to be sensitive to the anti-ERBB3 antibody that is identified by
   (i) measuring NRG1 gene expression in a tissue sample from the tumor, thereby determining an NRG1 score based on NRG1 expression alone; and
   (ii) determining that the NRG1 score is equal to or above a threshold score defined by a threshold determination analysis, indicating that, based on the NRG1 score alone, the tumor is likely to be responsive to treatment with the anti-ERBB3 antibody,
   wherein the anti-ERBB3 antibody is selected from the group consisting of:
   (a) (i) an immunoglobulin heavy chain variable region comprising a $CDR_{H1}$ comprising the amino acid sequence of SEQ ID NO: 1, a $CDR_{H2}$ comprising the amino acid sequence of SEQ ID NO: 2, and a $CDR_{H3}$ comprising the amino acid sequence of SEQ ID NO: 3; and
   (ii) an immunoglobulin light chain variable region comprising a $CDR_{L1}$ comprising the amino acid sequence of SEQ ID NO: 4, a $CDR_{L2}$ comprising the amino acid sequence of SEQ ID NO: 5, and a $CDR_{L3}$ comprising the amino acid sequence of SEQ ID NO: 6;
   (b) (i) an immunoglobulin heavy chain variable region comprising a $CDR_{H1}$ comprising the amino acid sequence of SEQ ID NO: 11, a $CDR_{H2}$ comprising the amino acid sequence of SEQ ID NO: 12, and a $CDR_{H3}$ comprising the amino acid sequence of SEQ ID NO: 13; and
   (ii) an immunoglobulin light chain variable region comprising a $CDR_{L1}$ comprising the s amino acid sequence of SEQ ID NO: 14, a $CDR_{L2}$ comprising the amino acid sequence of SEQ ID NO: 15, and a $CDR_{L3}$ comprising the amino acid sequence of SEQ ID NO: 16;
   (c) (i) an immunoglobulin heavy chain variable region comprising a $CDR_{H1}$ comprising the amino acid sequence of SEQ ID NO: 40, a $CDR_{H2}$ comprising the amino acid sequence of SEQ ID NO: 41, and a $CDR_{H3}$ comprising the amino acid sequence of SEQ ID NO: 42; and
   (ii) an immunoglobulin light chain variable region comprising a $CDR_{L1}$ comprising the amino acid sequence of SEQ ID NO: 14, a $CDR_{L2}$ comprising the amino acid sequence of SEQ ID NO: 15, and a $CDR_{L3}$ comprising the amino acid sequence of SEQ ID NO: 16;
   (d) (i) an immunoglobulin heavy chain variable region comprising a $CDR_{H1}$ comprising the amino acid sequence of SEQ ID NO: 47, a $CDR_{H2}$ comprising the amino acid sequence of SEQ ID NO: 48, and a $CDR_{H3}$ comprising the amino acid sequence of SEQ ID NO: 49; and
   (ii) an immunoglobulin light chain variable region comprising a $CDR_{L1}$ comprising the amino acid sequence of SEQ ID NO: 50, a $CDR_{L2}$ comprising the amino acid sequence of SEQ ID NO: 51, and a CDR$_{L3}$ comprising the amino acid sequence of SEQ ID NO: 52;
(e) (i) an immunoglobulin heavy chain variable region comprising a CDR$_{H1}$ comprising the amino acid sequence of SEQ ID NO: 57, a CDR$_{H2}$ comprising the amino acid sequence of SEQ ID NO: 58, and a CDR$_{H3}$ comprising the amino acid sequence of SEQ ID NO: 42; and
(ii) an immunoglobulin light chain variable region comprising a CDR$_{L1}$ comprising the amino acid sequence of SEQ ID NO: 14, a CDR$_{L2}$ comprising the amino acid sequence of SEQ ID NO: 15, and a CDR$_{L3}$ comprising the amino acid sequence of SEQ ID NO: 16;
(f) an immunoglobulin heavy chain variable region comprising the amino acid sequence of SEQ ID NO: 7, and an immunoglobulin light chain variable region comprising the amino acid sequence of SEQ ID NO: 8;
(g) an immunoglobulin heavy chain comprising the amino acid sequence of SEQ ID NO: 9, and an immunoglobulin light chain comprising the amino acid sequence of SEQ ID NO: 10;
(h) an immunoglobulin heavy chain variable region comprising the amino acid sequence of SEQ ID NO: 17, and an immunoglobulin light chain variable region comprising the amino acid sequence of SEQ ID NO: 18;
(i) an immunoglobulin heavy chain variable region comprising the amino acid sequence of SEQ ID NO: 43, and an immunoglobulin light chain variable region comprising the amino acid sequence of SEQ ID NO: 44;
(j) an immunoglobulin heavy chain variable region comprising the amino acid sequence of SEQ ID NO: 53, and an immunoglobulin light chain variable region comprising the amino acid sequence of SEQ ID NO: 54; and
(k) an immunoglobulin heavy chain variable region comprising the amino acid sequence of SEQ ID NO: 59, and an immunoglobulin light chain variable region comprising the amino acid sequence of SEQ ID NO: 60.

2. The method of claim 1, wherein the anti-ERBB3 antibody comprises (i) an immunoglobulin heavy chain variable region comprising a CDR$_{H1}$ comprising the amino acid sequence of SEQ ID NO: 1, a CDR$_{H2}$ comprising the amino acid sequence of SEQ ID NO: 2, and a CDR$_{H3}$ comprising the amino acid sequence of SEQ ID NO: 3; and (ii) an immunoglobulin light chain variable region comprising a CDR$_{L1}$ comprising the amino acid sequence of SEQ ID NO: 4, a CDR$_{L2}$ comprising the amino acid sequence of SEQ ID NO: 5, and a CDR$_{L3}$ comprising the amino acid sequence of SEQ ID NO: 6.

3. The method of claim 1, wherein the anti-ERBB3 antibody comprises an immunoglobulin heavy chain variable region comprising the amino acid sequence of SEQ ID NO: 7, and an immunoglobulin light chain variable region comprising the amino acid sequence of SEQ ID NO: 8.

4. The method of claim 1, wherein the anti-ERBB3 antibody comprises an immunoglobulin heavy chain comprising the amino acid sequence of SEQ ID NO: 9, and an immunoglobulin light chain comprising the amino acid sequence of SEQ ID NO: 10.

5. The method of claim 1, wherein the step of measuring NRG1 gene expression is performed by measuring the level of NRG1 protein.

6. The method of claim 1, wherein the step of measuring NRG1 gene expression is performed by measuring the level of mRNA encoding NRG1 protein.

7. The method of claim 1, wherein the threshold determination analysis comprises a receiver operator characteristic curve analysis.

8. The method of claim 1, wherein the tumor is a solid tumor.

* * * * *

UNITED STATES PATENT AND TRADEMARK OFFICE
CERTIFICATE OF CORRECTION

PATENT NO. : 9,828,635 B2
APPLICATION NO. : 14/349916
DATED : November 28, 2017
INVENTOR(S) : Sylvie Vincent et al.

Page 1 of 1

It is certified that error appears in the above-identified patent and that said Letters Patent is hereby corrected as shown below:

In Claim 1, at Column 72, Line 44, replace "the s amino acid sequence" with --the amino acid sequence--.

Signed and Sealed this
Sixth Day of March, 2018

Andrei Iancu
*Director of the United States Patent and Trademark Office*

SEQUENCE LISTING

```
<160> NUMBER OF SEQ ID NOS: 62

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Thr Ile Ser Asp Gly Gly Thr Tyr Thr Tyr Tyr Pro Asp Ser Val Lys
1               5                   10                  15
Gly

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Trp Gly Asp Tyr Asp Gly Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Glu Ile Ser Gly Tyr Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ala Ser Thr Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Tyr Asp Ser Tyr Pro Tyr Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

Ala Met Ser Trp Ile Arg Gln Ala Pro Gly Lys Gly Leu Glu Trp Val
            35                  40                  45

Ser Thr Ile Ser Asp Gly Gly Thr Tyr Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Trp Gly Asp Tyr Asp Gly Phe Asp Tyr Trp Gly Gln Gly
            100                 105                 110

Thr Leu Val Thr Val Ser Ser
            115

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Ser Gly Tyr
             20                  25                  30

Leu Ser Trp Tyr Gln Gln Lys Pro Gly Lys Ala Pro Lys Arg Leu Ile
         35                  40                  45

Tyr Ala Ala Ser Thr Leu Asp Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asp Ser Tyr Pro Tyr
                 85                  90                  95

Thr Phe Gly Gln Gly Thr Lys Leu Glu Ile Lys
            100                 105

<210> SEQ ID NO 9
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Met Arg Val Pro Ala Gln Leu Leu Gly Leu Leu Leu Leu Trp
 1               5                  10                  15

Leu Arg Gly Ala Arg Cys Gln Val Gln Leu Val Glu Ser Gly Gly Gly
             20                  25                  30

Leu Val Lys Pro Gly Gly Ser Leu Arg Leu Ser Cys Ala Ala Ser Gly
         35                  40                  45

Phe Thr Phe Ser Asp Tyr Ala Met Ser Trp Ile Arg Gln Ala Pro Gly
 50                  55                  60

Lys Gly Leu Glu Trp Val Ser Thr Ile Ser Asp Gly Gly Thr Tyr Thr
 65                  70                  75                  80

Tyr Tyr Pro Asp Ser Val Lys Gly Arg Phe Thr Ile Ser Arg Asp Asn
                 85                  90                  95

```
Ala Lys Asn Ser Leu Tyr Leu Gln Met Asn Ser Leu Arg Ala Glu Asp
            100                 105                 110

Thr Ala Val Tyr Tyr Cys Ala Arg Glu Trp Gly Asp Tyr Asp Gly Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 10
<211> LENGTH: 236
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 10

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Glu Ile Ser Gly Tyr Leu Ser Trp Tyr Gln Gln Lys Pro Gly Lys
    50                  55                  60

Ala Pro Lys Arg Leu Ile Tyr Ala Ala Ser Thr Leu Asp Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

Tyr Asp Ser Tyr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser His Trp Leu His
1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Leu Asp Pro Ser Asp Phe Tyr Ser Asn Tyr Asn Gln Asn Phe Lys
1               5                   10                  15

Gly

```
<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Leu Ser Gly Asp Tyr Ala Met Asp Tyr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Ser Gln Ser Ile Val His Ser Asn Gly Asn Thr Tyr Leu Glu
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Val Ser Asn Arg Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Gln Gly Ser Tyr Val Pro Trp Thr
1               5

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser His
            20                  25                  30

Trp Leu His Trp Val Lys Gln Arg Pro Gly Gln Gly Leu Glu Trp Ile
        35                  40                  45

Gly Val Leu Asp Pro Ser Asp Phe Tyr Ser Asn Tyr Asn Gln Asn Phe
    50                  55                  60
```

```
Lys Gly Lys Ala Thr Leu Thr Val Asp Thr Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Leu Leu Ser Gly Asp Tyr Ala Met Asp Tyr Trp Gly Gln
            100                 105                 110

Gly Thr Ser Val Thr Val Ser Ser
            115                 120
```

<210> SEQ ID NO 18
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Asp Val Leu Met Thr Gln Ile Pro Leu Ser Leu Pro Val Ser Leu Gly
 1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Ser Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Tyr Val Pro Trp Thr Phe Gly Gly Gly Thr Lys Leu Glu Ile Lys
            100                 105                 110
```

<210> SEQ ID NO 19
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Gly Trp Ser Cys Ile Ile Val Leu Leu Val Ser Thr Ala Thr Gly
 1               5                  10                  15

Val His Ser Gln Val Gln Leu Gln Gln Pro Gly Ala Glu Leu Val Arg
             20                  25                  30

Pro Gly Thr Ser Val Lys Leu Ser Cys Lys Ala Ser Gly Tyr Thr Phe
         35                  40                  45

Thr Ser His Trp Leu His Trp Val Lys Gln Arg Pro Gly Gln Gly Leu
 50                  55                  60

Glu Trp Ile Gly Val Leu Asp Pro Ser Asp Phe Tyr Ser Asn Tyr Asn
 65                  70                  75                  80

Gln Asn Phe Lys Gly Lys Ala Thr Leu Thr Val Asp Thr Ser Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Gly Leu Leu Ser Gly Asp Tyr Ala Met Asp Tyr
        115                 120                 125
```

```
Trp Gly Gln Gly Thr Ser Val Thr Val Ser Ser Ala Lys Thr Thr Pro
        130                 135                 140
Pro Ser Val Tyr Pro Leu Ala Pro Gly Ser Ala Ala Gln Thr Asn Ser
145                 150                 155                 160
Met Val Thr Leu Gly Cys Leu Val Lys Gly Tyr Phe Pro Glu Pro Val
                165                 170                 175
Thr Val Thr Trp Asn Ser Gly Ser Leu Ser Ser Gly Val His Thr Phe
            180                 185                 190
Pro Ala Val Leu Gln Ser Asp Leu Tyr Thr Leu Ser Ser Ser Val Thr
        195                 200                 205
Val Pro Ser Ser Thr Trp Pro Ser Gln Thr Val Thr Cys Asn Val Ala
210                 215                 220
His Pro Ala Ser Ser Thr Lys Val Asp Lys Lys Ile Val Pro Arg Asp
225                 230                 235                 240
Cys Gly Cys Lys Pro Cys Ile Cys Thr Val Pro Glu Val Ser Ser Val
                245                 250                 255
Phe Ile Phe Pro Pro Lys Pro Lys Asp Val Leu Thr Ile Thr Leu Thr
            260                 265                 270
Pro Lys Val Thr Cys Val Val Val Asp Ile Ser Lys Asp Asp Pro Glu
        275                 280                 285
Val Gln Phe Ser Trp Phe Val Asp Asp Val Glu Val His Thr Ala Gln
290                 295                 300
Thr Gln Pro Arg Glu Glu Gln Phe Asn Ser Thr Phe Arg Ser Val Ser
305                 310                 315                 320
Glu Leu Pro Ile Met His Gln Asp Trp Leu Asn Gly Lys Glu Phe Lys
                325                 330                 335
Cys Arg Val Asn Ser Ala Ala Phe Pro Ala Pro Ile Glu Lys Thr Ile
            340                 345                 350
Ser Lys Thr Lys Gly Arg Pro Lys Ala Pro Gln Val Tyr Thr Ile Pro
        355                 360                 365
Pro Pro Lys Glu Gln Met Ala Lys Asp Lys Val Ser Leu Thr Cys Met
370                 375                 380
Ile Thr Asp Phe Phe Pro Glu Asp Ile Thr Val Glu Trp Gln Trp Asn
385                 390                 395                 400
Gly Gln Pro Ala Glu Asn Tyr Lys Asn Thr Gln Pro Ile Met Asp Thr
                405                 410                 415
Asp Gly Ser Tyr Phe Val Tyr Ser Lys Leu Asn Val Gln Lys Ser Asn
            420                 425                 430
Trp Glu Ala Gly Asn Thr Phe Thr Cys Ser Val Leu His Glu Gly Leu
        435                 440                 445
His Asn His His Thr Glu Lys Ser Leu Ser His Ser Pro Gly Lys
450                 455                 460

<210> SEQ ID NO 20
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Leu Pro Val Arg Leu Leu Val Leu Met Phe Trp Ile Pro Ala
1               5                   10                  15
Ser Ser Ser Asp Val Leu Met Thr Gln Ile Pro Leu Ser Leu Pro Val
            20                  25                  30
```

-continued

```
Ser Leu Gly Asp Gln Ala Ser Ile Ser Cys Arg Ser Ser Gln Ser Ile
         35                  40                  45

Val His Ser Asn Gly Asn Thr Tyr Leu Glu Trp Tyr Leu Gln Lys Pro
 50                  55                  60

Gly Gln Ser Pro Lys Ser Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys
225                 230                 235

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Phe Gly Leu Ser Val Gly
1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

His Ile Trp Trp Asp Asp Asp Lys Tyr Tyr Asn Pro Ala Leu Lys Ser
1               5                   10                  15

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

```
Ile Gly Ala Asp Ala Leu Pro Phe Asp Tyr
 1               5                  10
```

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Arg Ser Ser Lys Ser Leu Leu His Ser Asn Gly Asn Thr Tyr Leu Tyr
 1               5                  10                  15
```

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Arg Met Ser Asn Leu Ala Ser
 1               5
```

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Met Gln His Leu Glu Tyr Pro Phe Thr
 1               5
```

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gln Val Thr Leu Lys Glu Ser Gly Pro Gly Ile Leu Arg Pro Ser Gln
 1               5                  10                  15

Thr Leu Ser Leu Thr Cys Ser Phe Ser Gly Phe Ser Leu Ser Thr Phe
                20                  25                  30

Gly Leu Ser Val Gly Trp Ile Arg Gln Pro Ser Gly Lys Gly Leu Glu
            35                  40                  45

Trp Leu Ala His Ile Trp Trp Asp Asp Lys Tyr Tyr Asn Pro Ala
        50                  55                  60

Leu Lys Ser Arg Leu Thr Ile Ser Lys Asp Thr Ser Lys Asn Gln Val
 65                 70                  75                  80

Phe Leu Lys Ile Ala Asn Val Asp Thr Ala Asp Thr Ala Thr Tyr Tyr
                85                  90                  95

Cys Ala Arg Ile Gly Ala Asp Ala Leu Pro Phe Asp Tyr Trp Gly Gln
            100                 105                 110

Gly Thr Thr Leu Thr Val Ser Ser
        115                 120
```

```
<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Leu Thr Gln Thr Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

<210> SEQ ID NO 29
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Arg
            20                  25                  30

Pro Ser Gln Thr Leu Ser Leu Thr Cys Ser Phe Ser Gly Phe Ser Leu
        35                  40                  45

Ser Thr Phe Gly Leu Ser Val Gly Trp Ile Arg Gln Pro Ser Gly Lys
    50                  55                  60

Gly Leu Glu Trp Leu Ala His Ile Trp Trp Asp Asp Lys Tyr Tyr
65                  70                  75                  80

Asn Pro Ala Leu Lys Ser Arg Leu Thr Ile Ser Lys Asp Thr Ser Lys
                85                  90                  95

Asn Gln Val Phe Leu Lys Ile Ala Asn Val Asp Thr Ala Asp Thr Ala
            100                 105                 110

Thr Tyr Tyr Cys Ala Arg Ile Gly Ala Asp Ala Leu Pro Phe Asp Tyr
        115                 120                 125

Trp Gly Gln Gly Thr Thr Leu Thr Val Ser Ser Ala Lys Thr Thr Pro
    130                 135                 140

Pro Ser Val Tyr Pro Leu Ala Pro Gly Cys Gly Asp Thr Thr Gly Ser
145                 150                 155                 160

Ser Val Thr Ser Gly Cys Leu Val Lys Gly Tyr Phe Pro Glu Pro Val
                165                 170                 175

Thr Val Thr Trp Asn Ser Gly Ser Leu Ser Ser Val His Thr Phe
            180                 185                 190
```

-continued

Pro Ala Leu Leu Gln Ser Gly Leu Tyr Thr Met Ser Ser Val Thr
         195                 200                 205

Val Pro Ser Ser Thr Trp Pro Ser Gln Thr Val Thr Cys Ser Val Ala
210                 215                 220

His Pro Ala Ser Ser Thr Thr Val Asp Lys Lys Leu Glu Pro Ser Gly
225                 230                 235                 240

Pro Ile Ser Thr Ile Asn Pro Cys Pro Pro Cys Lys Glu Cys His Lys
                245                 250                 255

Cys Pro Ala Pro Asn Leu Glu Gly Gly Pro Ser Val Phe Ile Phe Pro
            260                 265                 270

Pro Asn Ile Lys Asp Val Leu Met Ile Ser Leu Thr Pro Lys Val Thr
                275                 280                 285

Cys Val Val Val Asp Val Ser Glu Asp Asp Pro Asp Val Gln Ile Ser
            290                 295                 300

Trp Phe Val Asn Asn Val Glu Val His Thr Ala Gln Thr Gln Thr His
305                 310                 315                 320

Arg Glu Asp Tyr Asn Ser Thr Ile Arg Val Val Ser Thr Leu Pro Ile
                325                 330                 335

Gln His Gln Asp Trp Met Ser Gly Lys Glu Phe Lys Cys Lys Val Asn
            340                 345                 350

Asn Lys Asp Leu Pro Ser Pro Ile Glu Arg Thr Ile Ser Lys Ile Lys
        355                 360                 365

Gly Leu Val Arg Ala Pro Gln Val Tyr Thr Leu Pro Pro Pro Ala Glu
    370                 375                 380

Gln Leu Ser Arg Lys Asp Val Ser Leu Thr Cys Leu Val Val Gly Phe
385                 390                 395                 400

Asn Pro Gly Asp Ile Ser Val Glu Trp Thr Ser Asn Gly His Thr Glu
                405                 410                 415

Glu Asn Tyr Lys Asp Thr Ala Pro Val Leu Asp Ser Asp Gly Ser Tyr
            420                 425                 430

Phe Ile Tyr Ser Lys Leu Asn Met Lys Thr Ser Lys Trp Glu Lys Thr
        435                 440                 445

Asp Ser Phe Ser Cys Asn Val Arg His Glu Gly Leu Lys Asn Tyr Tyr
    450                 455                 460

Leu Lys Lys Thr Ile Ser Arg Ser Pro Gly Lys
465                 470                 475

<210> SEQ ID NO 30
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Arg Cys Leu Ala Glu Phe Leu Gly Leu Leu Val Leu Trp Ile Pro
1               5                   10                  15

Gly Ala Ile Gly Asp Ile Val Leu Thr Gln Thr Ala Pro Ser Val Pro
            20                  25                  30

Val Thr Pro Gly Glu Ser Val Ser Ile Ser Cys Arg Ser Ser Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala

```
                65                  70                  75                  80
Ser Gly Val Pro Asp Arg Phe Ser Gly Ser Gly Ser Gly Thr Ala Phe
                    85                  90                  95

Thr Leu Arg Ile Ser Arg Val Glu Ala Glu Asp Val Gly Val Tyr Tyr
                    100                 105                 110

Cys Met Gln His Leu Glu Tyr Pro Phe Thr Phe Gly Ser Gly Thr Lys
                    115                 120                 125

Leu Glu Ile Lys Arg Ala Asp Ala Ala Pro Thr Val Ser Ile Phe Pro
        130                 135                 140

Pro Ser Glu Gln Leu Thr Ser Gly Gly Ala Ser Val Val Cys Phe
145                 150                 155                 160

Leu Asn Asn Phe Tyr Pro Arg Asp Ile Asn Val Lys Trp Lys Ile Asp
                    165                 170                 175

Gly Ser Glu Arg Gln Asn Gly Val Leu Asn Ser Trp Thr Asp Gln Asp
                    180                 185                 190

Ser Lys Asp Ser Thr Tyr Ser Met Ser Ser Thr Leu Thr Leu Thr Lys
                    195                 200                 205

Asp Glu Tyr Glu Arg His Asn Ser Tyr Thr Cys Glu Ala Thr His Lys
        210                 215                 220

Thr Ser Thr Ser Pro Ile Val Lys Ser Phe Asn Arg Asn Glu Cys
225                 230                 235

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp His Ile Ile His
1               5

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Ile Tyr Pro Arg Asp Gly Tyr Ile Lys Tyr Asn Glu Lys Phe Lys
1               5                   10                  15

Gly

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Tyr Tyr Tyr Ala Met Asp Tyr
1               5

<210> SEQ ID NO 34
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ser Ser Gln Ser Ile Val His Ser Ile Gly Asn Thr Tyr Leu Glu
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gln Gly Ser His Val Pro Phe Thr
1               5

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
                20                  25                  30

Ile Ile His Trp Met Lys Gln Arg Pro Glu Gln Gly Leu Glu Trp Ile
            35                  40                  45

Gly Tyr Ile Tyr Pro Arg Asp Gly Tyr Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Val Asn Ser Leu Thr Ser Glu Asp Ser Ala Val Tyr Phe Cys
                85                  90                  95

Ala Arg Gly Tyr Tyr Tyr Ala Met Asp Tyr Trp Gly Gln Gly Thr Ser
            100                 105                 110

Val Thr Val Ser Ser
        115

<210> SEQ ID NO 37
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Ile Gly Asn Thr Tyr Leu Glu Trp Tyr Leu Gln Lys Pro Gly Gln Ser
            35                  40                  45
```

```
Pro Lys Leu Leu Ile Tyr Lys Val Ser Asn Arg Phe Ser Gly Val Pro
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```

<210> SEQ ID NO 38
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Glu Trp Ser Trp Val Ser Leu Phe Phe Leu Ser Val Thr Thr Gly
1               5                   10                  15

Val His Ser Gln Val Gln Leu Gln Gln Ser Asp Ala Glu Leu Val Lys
                20                  25                  30

Pro Gly Ala Ser Val Lys Ile Ser Cys Lys Val Ser Gly Tyr Thr Phe
            35                  40                  45

Thr Asp His Ile Ile His Trp Met Lys Gln Arg Pro Glu Gln Gly Leu
        50                  55                  60

Glu Trp Ile Gly Tyr Ile Tyr Pro Arg Asp Gly Tyr Ile Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Val Asn Ser Leu Thr Ser Glu Asp Ser Ala Val
            100                 105                 110

Tyr Phe Cys Ala Arg Gly Tyr Tyr Tyr Ala Met Asp Tyr Trp Gly Gln
        115                 120                 125

Gly Thr Ser Val Thr Val Ser Ser Ala Lys Thr Thr Pro Pro Ser Val
130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Gln Thr Val Thr Cys Asn Val Ala His Pro Ala
210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
```

```
                290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
                420                 425                 430

Gly Asn Thr Phe Thr Cys Ser Val Leu His Glu Gly Leu His Asn His
            435                 440                 445

His Thr Glu Lys Ser Leu Ser His Ser Pro Gly Lys
        450                 455                 460

<210> SEQ ID NO 39
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Lys Leu Pro Val Arg Leu Leu Val Leu Met Phe Trp Ile Pro Ala
1               5                   10                  15

Ser Arg Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Ile
            35                  40                  45

Val His Ser Ile Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Glu Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190
```

```
Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Ser Tyr Trp Met His
1               5
```

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Met Ile Asp Pro Ser Asp Val Tyr Thr Asn Tyr Asn Pro Lys Phe Lys
1               5                   10                  15

Gly
```

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Asn Tyr Ser Gly Asp Tyr
1               5
```

<210> SEQ ID NO 43
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gln Val Gln Leu Leu Gln Pro Gly Ala Glu Leu Val Arg Pro Gly Thr
1               5                   10                  15

Ser Val Lys Leu Ser Cys Lys Thr Ser Gly Tyr Thr Phe Ser Ser Tyr
            20                  25                  30

Trp Met His Trp Val Lys Gln Arg Pro Gly Gln Gly Leu Glu Trp Ile
        35                  40                  45

Gly Met Ile Asp Pro Ser Asp Val Tyr Thr Asn Tyr Asn Pro Lys Phe
    50                  55                  60

Lys Gly Lys Ala Thr Leu Thr Val Asp Thr Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Arg Asn Tyr Ser Gly Asp Tyr Trp Gly Gln Gly Thr Thr Leu Thr
            100                 105                 110

Val Ser Ser
        115

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Val Pro Trp Thr Phe Gly Gly Gly Thr Lys Leu Glu Ile Lys
            100                 105                 110

<210> SEQ ID NO 45
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Trp Ser Cys Ile Ile Val Leu Leu Val Ser Thr Ala Thr Cys
1               5                   10                  15

Val His Ser Gln Val Gln Leu Leu Gln Pro Gly Ala Glu Leu Val Arg
            20                  25                  30

Pro Gly Thr Ser Val Lys Leu Ser Cys Lys Thr Ser Gly Tyr Thr Phe
        35                  40                  45

Ser Ser Tyr Trp Met His Trp Val Lys Gln Arg Pro Gly Gln Gly Leu
    50                  55                  60

Glu Trp Ile Gly Met Ile Asp Pro Ser Asp Val Tyr Thr Asn Tyr Asn
65                  70                  75                  80

Pro Lys Phe Lys Gly Lys Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Asn Tyr Ser Gly Asp Tyr Trp Gly Gln Gly Thr
        115                 120                 125

Thr Leu Thr Val Ser Ser Ala Lys Thr Thr Pro Pro Ser Val Tyr Pro
    130                 135                 140
```

```
Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
            165                 170                 175

Ser Gly Ser Leu Ser Ser Gly Val His Thr Phe Pro Ala Val Leu Gln
        180                 185                 190

Ser Asp Leu Tyr Thr Leu Ser Ser Val Thr Val Pro Ser Ser Thr
    195                 200                 205

Trp Pro Ser Gln Thr Val Thr Cys Asn Val Ala His Pro Ala Ser Ser
210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
            245                 250                 255

Lys Pro Lys Asp Val Leu Thr Ile Thr Leu Thr Pro Lys Val Thr Cys
        260                 265                 270

Val Val Val Asp Ile Ser Lys Asp Asp Pro Glu Val Gln Phe Ser Trp
    275                 280                 285

Phe Val Asp Asp Val Glu Val His Thr Ala Gln Thr Gln Pro Arg Glu
290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
            325                 330                 335

Ala Ala Phe Pro Ala Pro Ile Glu Lys Thr Ile Ser Lys Thr Lys Gly
        340                 345                 350

Arg Pro Lys Ala Pro Gln Val Tyr Thr Ile Pro Pro Pro Lys Glu Gln
    355                 360                 365

Met Ala Lys Asp Lys Val Ser Leu Thr Cys Met Ile Thr Asp Phe Phe
370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asp Thr Asp Gly Ser Tyr Phe
            405                 410                 415

Val Tyr Ser Lys Leu Asn Val Gln Lys Ser Asn Trp Glu Ala Gly Asn
        420                 425                 430

Thr Phe Thr Cys Ser Val Leu His Glu Gly Leu His Asn His His Thr
    435                 440                 445

Glu Lys Ser Leu Ser His Ser Pro Gly Lys
450                 455

<210> SEQ ID NO 46
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Lys Leu Pro Val Arg Leu Leu Val Leu Met Phe Trp Ile Pro Ala
1               5                   10                  15

Ser Ser Ser Asp Val Leu Met Thr Gln Ile Pro Leu Ser Leu Pro Val
            20                  25                  30

Ser Leu Gly Asp Gln Ala Ser Ile Ser Cys Arg Ser Ser Gln Ser Ile
        35                  40                  45
```

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Tyr Gly Met Ser
1               5

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Ile Asn Thr Tyr Ser Gly Val Pro Thr Tyr Ala Asp Asp Phe Lys
1               5                   10                  15

Gly

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Arg Asp Gly Tyr Gln Val Ala Trp Phe Ala Tyr

```
<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Thr Ser Thr Asp Ile Asp Asp Asp Met Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Gly Asn Thr Leu Arg Pro
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Gln Ser Asp Asn Leu Pro Tyr Thr
1               5

<210> SEQ ID NO 53
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ile Gln Leu Val Gln Ser Gly Pro Glu Leu Lys Lys Pro Gly Glu
1               5                   10                  15

Ala Val Lys Ile Ser Cys Lys Ser Ser Gly Tyr Thr Phe Thr Thr Tyr
            20                  25                  30

Gly Met Ser Trp Val Lys Gln Ala Pro Gly Arg Ala Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Ser Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Arg Asp Gly Tyr Gln Val Ala Trp Phe Ala Tyr Trp Gly
            100                 105                 110

Gln Gly Thr Leu Val Thr Val Ser Ala
        115                 120
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Thr Thr Val Thr Gln Ser Pro Ala Ser Leu Ser Met Ala Ile Gly
1               5                   10                  15

Asp Lys Val Thr Ile Arg Cys Ile Thr Ser Thr Asp Ile Asp Asp Asp
                20                  25                  30

Met Asn Trp Phe Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Gly
        50                  55                  60

Ser Gly Tyr Gly Thr Asp Phe Ile Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105

<210> SEQ ID NO 55
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
                20                  25                  30

Pro Gly Glu Ala Val Lys Ile Ser Cys Lys Ser Ser Tyr Thr Phe Phe
            35                  40                  45

Thr Thr Tyr Gly Met Ser Trp Val Lys Gln Ala Pro Gly Arg Ala Leu
        50                  55                  60

Lys Trp Met Gly Trp Ile Asn Thr Tyr Ser Gly Val Pro Thr Tyr Ala
65                  70                  75                  80

Asp Asp Phe Lys Gly Arg Phe Ala Phe Ser Leu Glu Ser Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Gly Arg Asp Gly Tyr Gln Val Ala Trp Phe Ala
            115                 120                 125

Tyr Trp Gly Gln Gly Thr Leu Val Thr Val Ser Ala Ala Lys Thr Thr
        130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

```
Phe Pro Ala Val Leu Gln Ser Asp Leu Tyr Thr Leu Ser Ser Val
            195                 200                 205

Thr Val Pro Ser Ser Thr Trp Pro Ser Gln Thr Val Thr Cys Asn Val
        210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
450                 455                 460

<210> SEQ ID NO 56
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Phe Ser Leu Ala Leu Leu Ser Leu Leu Leu Leu Cys Val Ser
1               5                   10                  15

Asp Ser Arg Ala Glu Thr Thr Val Thr Gln Ser Pro Ala Ser Leu Ser
            20                  25                  30

Met Ala Ile Gly Asp Lys Val Thr Ile Arg Cys Ile Thr Ser Thr Asp
        35                  40                  45

Ile Asp Asp Asp Met Asn Trp Phe Gln Gln Lys Pro Gly Glu Pro Pro
50                  55                  60

Lys Leu Leu Ile Ser Glu Gly Asn Thr Leu Arg Pro Gly Val Pro Ser
65                  70                  75                  80

Arg Phe Ser Gly Ser Gly Tyr Gly Thr Asp Phe Ile Phe Thr Ile Glu
                85                  90                  95
```

```
Asn Met Leu Ser Glu Asp Val Ala Asp Tyr Tyr Cys Leu Gln Ser Asp
                100                 105                 110

Asn Leu Pro Tyr Thr Phe Gly Gly Thr Lys Leu Glu Ile Lys Arg
            115                 120                 125

Ala Asp Ala Ala Pro Thr Val Ser Ile Phe Pro Pro Ser Ser Glu Gln
            130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
            210                 215                 220

Ile Val Lys Ser Phe Asn Arg Asn Glu Cys
225                 230

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Tyr Trp Met His
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Met Ile Asp Pro Ser Asp Ser Tyr Thr Asn Tyr Asn Pro Lys Phe Lys
1               5                   10                  15

Gly

<210> SEQ ID NO 59
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Asn Tyr
                20                  25                  30

Trp Met His Trp Val Lys Gln Arg Pro Gly Gln Gly Leu Glu Trp Ile
            35                  40                  45

Gly Met Ile Asp Pro Ser Asp Ser Tyr Thr Asn Tyr Asn Pro Lys Phe
```

```
            50                  55                  60
Lys Gly Lys Ala Thr Leu Thr Val Asp Thr Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asn Tyr Ser Gly Asp Tyr Trp Gly Gln Gly Thr Leu Thr
                100                 105                 110

Val Ser Ser
        115

<210> SEQ ID NO 60
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Tyr Val Pro Trp Thr Phe Gly Gly Gly Thr Lys Leu Glu Ile Lys
                100                 105                 110

<210> SEQ ID NO 61
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Gly Trp Ser Cys Ile Ile Leu Val Leu Val Ser Thr Ala Thr Gly
  1               5                  10                  15

Val His Ser Gln Val Gln Leu Gln Gln Pro Gly Ala Glu Leu Val Arg
             20                  25                  30

Pro Gly Thr Ser Val Lys Leu Ser Cys Lys Ala Ser Gly Tyr Thr Phe
         35                  40                  45

Thr Asn Tyr Trp Met His Trp Val Lys Gln Arg Pro Gly Gln Gly Leu
 50                  55                  60

Glu Trp Ile Gly Met Ile Asp Pro Ser Asp Ser Tyr Thr Asn Tyr Asn
 65                  70                  75                  80

Pro Lys Phe Lys Gly Lys Ala Thr Leu Thr Val Asp Thr Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Asn Tyr Ser Gly Asp Tyr Trp Gly Gln Gly Thr
```

```
            115                 120                 125
Thr Leu Thr Val Ser Ser Ala Lys Thr Thr Pro Pro Ser Val Tyr Pro
        130                 135                 140
Leu Ala Pro Gly Ser Ala Ala Gln Thr Asn Ser Met Val Thr Leu Gly
145                 150                 155                 160
Cys Leu Val Lys Gly Tyr Phe Pro Glu Pro Val Thr Val Thr Trp Asn
                165                 170                 175
Ser Gly Ser Leu Ser Ser Gly Val His Thr Phe Pro Ala Val Leu Gln
            180                 185                 190
Ser Asp Leu Tyr Thr Leu Ser Ser Val Thr Val Pro Ser Ser Thr
        195                 200                 205
Trp Pro Ser Gln Thr Val Thr Cys Asn Val Ala His Pro Ala Ser Ser
210                 215                 220
Thr Lys Val Asp Lys Lys Ile Val Pro Arg Asp Cys Gly Cys Lys Pro
225                 230                 235                 240
Cys Ile Cys Thr Val Pro Glu Val Ser Ser Val Phe Ile Phe Pro Pro
                245                 250                 255
Lys Pro Lys Asp Val Leu Thr Ile Thr Leu Thr Pro Lys Val Thr Cys
            260                 265                 270
Val Val Val Asp Ile Ser Lys Asp Asp Pro Glu Val Gln Phe Ser Trp
        275                 280                 285
Phe Val Asp Asp Val Glu Val His Thr Ala Gln Thr Gln Pro Arg Glu
290                 295                 300
Glu Gln Phe Asn Ser Thr Phe Arg Ser Val Ser Glu Leu Pro Ile Met
305                 310                 315                 320
His Gln Asp Trp Leu Asn Gly Lys Glu Phe Lys Cys Arg Val Asn Ser
                325                 330                 335
Ala Ala Phe Pro Ala Pro Ile Glu Lys Thr Ile Ser Lys Thr Lys Gly
            340                 345                 350
Arg Pro Lys Ala Pro Gln Val Tyr Thr Ile Pro Pro Pro Lys Glu Gln
        355                 360                 365
Met Ala Lys Asp Lys Val Ser Leu Thr Cys Met Ile Thr Asp Phe Phe
370                 375                 380
Pro Glu Asp Ile Thr Val Glu Trp Gln Trp Asn Gly Gln Pro Ala Glu
385                 390                 395                 400
Asn Tyr Lys Asn Thr Gln Pro Ile Met Asp Thr Asp Gly Ser Tyr Phe
                405                 410                 415
Val Tyr Ser Lys Leu Asn Val Gln Lys Ser Asn Trp Glu Ala Gly Asn
            420                 425                 430
Thr Phe Thr Cys Ser Val Leu His Glu Gly Leu His Asn His His Thr
        435                 440                 445
Glu Lys Ser Leu Ser His Ser Pro Gly Lys
    450                 455

<210> SEQ ID NO 62
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Lys Leu Pro Val Arg Leu Leu Val Leu Met Phe Trp Ile Pro Ala
1               5                   10                  15
```

-continued

```
Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
 50                      55                  60

Gly Gln Ser Pro Lys Leu Leu Ile Tyr Lys Val Ser Asn Arg Phe Ser
 65              70                  75                      80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Tyr Val Pro Trp Thr Phe Gly Gly Gly Thr Lys Leu
            115                 120                 125

Glu Ile Lys Arg Ala Asp Ala Ala Pro Thr Val Ser Ile Phe Pro Pro
            130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
            210                 215                 220

Ser Thr Ser Pro Ile Val Lys Ser Phe Asn Arg Asn Glu Cys
225                 230                 235
```